(12) United States Patent
Iliopoulos et al.

(10) Patent No.: US 9,311,566 B2
(45) Date of Patent: Apr. 12, 2016

(54) METHOD AND SYSTEM FOR DIRECT STRAIN IMAGING

(71) Applicants: GEORGE MASON RESEARCH FOUNDATION, INC., Fairfax, VA (US); THE UNITED STATES OF AMERICA, AS REPRESENTED BY THE SECRETARY OF THE NAVY, Arlington, VA (US)

(72) Inventors: Athanasios Iliopoulos, Bethesda, MD (US); John G. Michopoulos, Washington, DC (US)

(73) Assignees: George Mason Research Foundation, Inc., Fairfax, VA (US); The United States of America, as Represented by the Secretary of the Navy, Washington, DC (US)

( * ) Notice: Subject to any disclaimer, the term of this patent is extended or adjusted under 35 U.S.C. 154(b) by 328 days.

(21) Appl. No.: 13/958,247

(22) Filed: Aug. 2, 2013

(65) Prior Publication Data
US 2014/0037217 A1    Feb. 6, 2014

Related U.S. Application Data

(60) Provisional application No. 61/679,120, filed on Aug. 3, 2012.

(51) Int. Cl.
*G06K 9/62*    (2006.01)
*G01N 3/06*    (2006.01)
(Continued)

(52) U.S. Cl.
CPC .............. *G06K 9/6232* (2013.01); *G01B 11/16* (2013.01); *G01N 3/068* (2013.01); *G06T 7/2046* (2013.01);
(Continued)

(58) Field of Classification Search
CPC ........ G06T 7/00; G06T 2207/30; G06K 9/62; G06K 9/00

USPC .......................................................... 382/201
See application file for complete search history.

(56) References Cited

U.S. PATENT DOCUMENTS 3,976,381 A    8/1976  Walker et al.
4,288,852 A    9/1981  Holland
(Continued)

FOREIGN PATENT DOCUMENTS

EP    0356727 A2    3/1990

OTHER PUBLICATIONS

Full-Field Displacement Measurement of a Speckle Grid by using a Mesh-Free Deformation Function. N. P. Andrianopoulos. 2006.*
(Continued)

*Primary Examiner* — Stephen R Koziol
*Assistant Examiner* — Delomia L Gilliard
(74) *Attorney, Agent, or Firm* — Eckert Seamans Cherin & Mellott, LLC; Philip E. Levy

(57) ABSTRACT

A method and system for measuring and determining the full-field spatial distributions of strain tensor field components in a two or three-dimensional space, as a consequence of deformation under generalized loading conditions. One or more digital cameras may be used to acquire successive images of a deforming body with optically distinctive features on its surface. A method for determining the location of characteristic points of the surface features and another one for tracking these points as deformation occurs. Elongations between neighboring points on the vicinity of a location of interest are computed. The elongation between points is calculated even though discontinuities may exist between them. Strain tensor fields are directly calculated as a tensor approximation from these elongations without determining or using the displacement vector distributions.

23 Claims, 11 Drawing Sheets

(Un-deformed)

(Deformed)

(51) Int. Cl.
*G06T 7/20* (2006.01)
*G01B 11/16* (2006.01)

(52) U.S. Cl.
CPC ...... *G06T 7/2086* (2013.01); *G01N 2203/0212* (2013.01); *G01N 2203/0647* (2013.01); *G06T 2207/10021* (2013.01); *G06T 2207/10024* (2013.01); *G06T 2207/30108* (2013.01)

(56) References Cited

U.S. PATENT DOCUMENTS

| | | | |
|---|---|---|---|
| 4,432,239 | A | 2/1984 | Bykov |
| 4,474,466 | A | 10/1984 | McDonach et al. |
| 4,598,420 | A | 7/1986 | Harvey |
| 4,690,552 | A | 9/1987 | Grant et al. |
| 4,765,189 | A | 8/1988 | Preater |
| 4,872,751 | A | 10/1989 | Hercher |
| 4,967,093 | A | 10/1990 | Takemori |
| 4,969,106 | A | 11/1990 | Vogel et al. |
| 5,166,742 | A | 11/1992 | Kobayashi et al. |
| 5,642,293 | A | 6/1997 | Manthey et al. |
| 5,671,042 | A | 9/1997 | Sciammarella |
| 5,726,907 | A | 3/1998 | Davidson et al. |
| 5,757,473 | A | 5/1998 | Kanduth et al. |
| 6,097,477 | A | 8/2000 | Sarrafzadeh-Khoee |
| 6,189,386 | B1 | 2/2001 | Chen et al. |
| 6,327,030 | B1 | 12/2001 | Ifju et al. |
| 6,563,129 | B1 | 5/2003 | Knobel |
| 6,584,215 | B1 | 6/2003 | Mahner |
| 6,934,013 | B2 | 8/2005 | Vachon et al. |
| 6,943,869 | B2 | 9/2005 | Hubner et al. |
| 7,377,181 | B2 | 5/2008 | Christ, Jr. et al. |
| 7,460,216 | B2 | 12/2008 | Lecomte et al. |
| 7,477,362 | B2 | 1/2009 | Asundi et al. |
| 7,512,502 | B1 | 3/2009 | Yoshida |
| 8,269,982 | B1 | 9/2012 | Olczak et al. |
| 8,363,977 | B2 | 1/2013 | Imaizumi |
| 2002/0052700 | A1 | 5/2002 | Shakespeare |
| 2007/0044568 | A1 | 3/2007 | Kobayashi |
| 2010/0310128 | A1* | 12/2010 | Iliopoulos et al. ............ 382/103 |
| 2011/0268312 | A1 | 11/2011 | Imaizumi |
| 2013/0063570 | A1* | 3/2013 | Michopoulos et al. ......... 348/47 |

OTHER PUBLICATIONS

Michopoulos, J.G., "Accuracy of Inverse Composite Laminate Characterization Via the Mesh Free Random Grid Method", IDETC/CIE 2009, pp. 1-8, Aug. 30-Sep. 2, 2009, San Diego, CA.
Michopoulos, J.G., "A Computational Workbench for Remote Full Field 2D Displacement and Strain Measurements", IDETC/CIE 2009, pp. 1-9, Aug. 30-Sep. 2, 2009, San Diego, CA.
Michopoulos, J.G., "A Computational Workbench for Remote Full Field 3D Displacement and Strain Measurements", IDETC/CIE 2011, pp. 1-9, Aug. 28-31, 2011, Washington,DC.
Liu, G.R., "A Local Radial Point Interpolation Method (LRPIM) for Free Vibration Analyses of 2-D Solids", Journal of Sound and Vibration (2001), 246(1), pp. 29-46.
Liu, G.R., "A Point Interpolation Method for Two Dimensional Solids", Intl Journal for Numerical Methods in Engineering 2001; vol. 50(4), pp. 937-951.
Iliopoulos, A.P., "An Approach to Analyze Errors Introduced in the Random Grid Strain Measurement Method", Strain, An Intl Journal for Experimental mechanics, pp. 1-9.
Andersen, K., "Calculation of Grating Coordinates Using a Correlation Filter Technique", Optik, vol. 80, No. 2, 1988, pp. 76-79.
Bruck, H.A., "Digital Image Correlation Using Newton-Raphson Method of Partial Differential Correction", Experimental Mechanics, pp. 261-267.
Peters, W.H., "Digital Imaging Techniques in Experimental Stress Analysis", Optical Engineering, May-Jun. 1982, vol. 21 No. 3 p. 427-431.

Iliopoulos A., "Digital Image Processing in Experimental Mechanics and applications to Metallic Sheets", Natl Technical Univ. of Athens School of applied Mathematics and Physics Section of Mechanics; Athens, 2007, pp. 1-3.
Iliopoulos, A., "Direct Strain Imaging for Full Field Measurements", IDETC/CIE, Aug. 12-15, 2012, Chicago, IL pp. 1-11.
Iliopoulos, A., "Direct Strain Tensor Approximation for Full Field Strain Measurement", Jul. 23, 2013, pp. 1-24.
Sirkis, J.S., "Displacement and Strain Measurement with Automated Grid Methods", Experimental Mechanics, Dec. 1991, pp. 382-388.
Michopoulos, J.G., "Draft: A Computational Workbench for Remote Full Field 2D Displacement and Strain Measurements", IDETC/CIE 2009, Aug. 30-Sep. 2, 2009; San Diego, CA., pp. 1-9.
Iliopoulos, A.P., Effects of Anisotropy on the performance Sensitivity of the Mesh-Free Random Grid Method for Whole Field Strain Measurement, IDETC/CIE 2009, Aug. 30-Sep. 2, 2009, San Diego, CA., pp. 1-10.
Factory, P.R., "Effects of Computational Technology on Composite Materials Research: The Case of Dissipated Energy Density", First Hellenic Conf. on Composite Materials Research, Jul. 2-5,Democritus University of Thrace, Xanthi, Greece, pp. 1-39.
Belytschko, T., "Element-Free Galerkin Methods", Intl Journal for Numerical Methods in Engineering, vol. 37, 1994, pp. 229-256.
Michopoulos, J.G., "First Industrial Strength Multi-Axial RoboticTesting Campaign for Composite Material Characterization", IDETC/CIE 2012, Aug. 12-15, 2012, Chicago, IL, pp. 1-11.
Andrianopoulos, N.P., "Full-Field Displacement Measurement of a Speckle Grid by Using a Mesh-Free Deformation Function", Dept. of Mechanics, Faculty of Applied Sciences, Nat'l Technical Univ. of Athens, Greece, pp. 1-7.
Chen, P., "Full-Field Speckle Pattern Image Correlation with B-Spline Deformation Function", Experimental Mechanics, vol. 42, No. 3, Sep. 2002, pp. 344-352.
Jin, H., "Grid Method for Microscale Discontinuous Deformation Measurement", Experimental Mechanics 2011, vol. 51, pp. 565-574.
Bruneel, H., "Intrinsic Errors on Sheet Strain Measurements Based on a printed Square Grid", Journal of Manufacturing Science and Engineering, Nov. 2000, vol. 122, pp. 760-765.
Iliopoulos, A., "Performance Analysis and Experimental Validation of the Direct Strain Imaging Method", Computational Materials Science Center, Fairfax,Va, pp. 1-20.
Iliopoulos, A.P., "Performance Analysis of he Mesh-Free Random Grid Method for Full-Field synthetic Strain Measurements", Strain, An Intl Journal for Experimental Mechanics, pp. 1-15.
Iliopoulos, A.P., "Performance Sensitivity Analysis of the Mesh-Free Random Grid Method for Whole Field Strain Measurements", IDETC/CIE 2008, Aug. 3-6, 2008, Brooklyn, New York, pp. 1-11.
Sevenhuijsen, P., "The Photonical, Pure Grid Method", Optics and Lasers in Engineering vol. 18, 1993, pp. 173-194, Elsevier Science Publishers Ltd. England.
Andrianopoulos, N.P., "Strain Measurements by a Hybrid Experimental-Numerical Method Using a Mesh-Free Field Function", Modern Problems of Deformable Bodies Mechanics, Collection of Papers, Yerevan 2005, pp. 31-41.
Parks, V.J., "Strain Measurement Using Grids", Optical Engineering, Jul.-Aug. 1982, vol. 21, No. 4, pp. 633-639.
Lancaster, P., "Surfaces Generated by Moving Least Squares Methods", Mathematics of Computation, vol. 37. No. 155, Jul. 1981, pp. 141-158.
Schreier, H.W., "Systematic Errors in Digital Image Correlation Caused by Intensity Interpolation", OpticalEngineering, vol. 39, No. 11, Nov. 2000, pp. 2915-2921.
Sirkis, J.S., "System Response to Automated Grid Methods", Optical Engineering, Dec. 1990, vol. 29, No. 12, pp. 1485-1493.
Michopoulos, J.G., "Towards a Recursive Hexapod for the Multidimensional Mechanical Testing of Composites", IDETC/CIE 2010, Aug. 15-18, 2010, Quebec, Canada, pp. 1-9.
Michopoulos, J.G., Towards the Robotic Characterization of the Constitutive Response of Composite Materials, Composite Structures, vol. 86, 2008, pp. 154-164.
Sevenhuijsen, P.J., Two Simple Methods for Deformation Demonstration and Measurement, Strain, Feb. 1981, pp. 20-24.

* cited by examiner

| Complete Order | No. of Terms | Additional Terms |
|---|---|---|
| Constant | 1 | 1 |
| Linear | 3 | $\left\{\dfrac{1}{2}(x_A+x_B), \dfrac{1}{2}(y_A+y_B)\right\}$ |
| Bi-linear | 4 | $\dfrac{1}{6}(x_A(2y_A+y_B)+x_B(y_A+2y_B))$ |
| Quadratic | 6 | $\left\{\dfrac{1}{3}(x_A x_B+x_A^2+x_B^2), \dfrac{1}{3}(y_A y_B+y_A^2+y_B^2)\right\}$ |
| *Quadratic | 2*8 | $\left\{\dfrac{1}{12}(x_A^2(3y_A+y_B)+2x_A x_B(y_A+y_B)+x_B^2(y_A+3y_B))\right.$ |
| | | $\left.\dfrac{1}{12}(y_A^2(3x_A+x_B)+2y_A y_B(x_A+x_B)+y_B^2(x_A+3x_B))\right\}$ |
| Cubic | 10 | $\left\{\dfrac{1}{4}(x_A+x_B)(x_A^2+x_B^2), \dfrac{1}{4}(y_A+y_B)(y_A^2+y_B^2)\right\}$ |
| *Quartic | 5*15 | $\left\{\dfrac{1}{20}(x_A^3(4y_A+y_B)+x_A^2 x_B(3y_A+2y_B)+x_A x_B^2(2y_A+3y_B)\right.$ |
| | | $+x_B^3(y_A+4y_B))$ |
| | | $\dfrac{1}{30}(x_A^2(3y_A y_B+6y_A^2+y_B^2)+x_A x_B(4y_A y_B+3y_A^2+3y_B^2)+$ |
| | | $+x_B^2(3y_A y_B+y_A^2+6y_B^2))$ |
| | | $\dfrac{1}{20}(y_A^3(4x_A+x_B)+y_A^2 y_B(3x_A+2x_B)+y_A y_B^2(2x_A+3x_B)+$ |
| | | $+y_B^3(x_A+4x_B))$ |
| | | $\dfrac{1}{5}(x_A^3 x_B+x_A^2 x_B^2+x_A x_B^3+x_A^4+x_B^4)$ |
| | | $\left.\dfrac{1}{5}(y_A^3 y_B+y_A^2 y_B^2+y_A y_B^3+y_A^4+y_B^4)\right\}$ |

FIG. 4

METHOD AND SYSTEM FOR DIRECT STRAIN IMAGING

CROSS-REFERENCE TO RELATED APPLICATIONS

This application claims the benefit of U.S. Provisional Patent Application No. 61/679,120, filed Aug. 3, 2012, which is hereby incorporated in its entirety.

STATEMENT REGARDING GOVERNMENT SUPPORT

This invention was made with government support under contract N00173-11-1G002 awarded by the United States Navy. The government has certain rights in the invention."

FIELD OF THE INVENTION

The present system and method relate generally to the determination of strain in a deforming body, and more specifically, to a method, system, and a corresponding set of tools for the data acquisition, digital image processing; field variable approximation or interpolation and visualization of digital images of a deforming body in two or three dimensions for a direct determination of strain tensor component fields without a need to determine displacement fields.

BACKGROUND

Digital imaging has been used to measure the deformation of deformable material specimens and structures. These displacement measurement methods have gained significant attention the last two decades, because of the great impact of digital imaging evolution. Modern digital cameras provide a cost effective and highly reliable tool for recording and processing images of an experiment using a personal computer. Experimental mechanics have greatly benefited from those capabilities, and various methods have been developed for the determination of displacement and strain fields.

Both pure grid methods and digital image correlation methods have been proposed for providing full-field measurements of displacement and strains.

In pure grid methods, a uniform grid is applied to the surface of a specimen, and the measurement of deformation relies on the motion of the grid. Many of these methods rely on specialized means for application of a uniform grid. It can be difficult to apply a uniform grid to irregularly shaped bodies, and any inaccuracies in the application of the grid are a major source of errors in the measurement of deformation.

Pure grid methods are described in Sevenhuijsen, P. J., "Two simple methods for deformation demonstration and measurement", Strain, Vol. 17, pp. 20-24 (1981); Parks, V. J., "Strain measurements using grids", Opt. Eng., Vol. 21, pp. 633-639 (1982); Sevenhuijsen, P. J., "Photonics for deformations", Proc 5th Int. Congr. On Expt. Mechanics, SESA, Montreal, (June 1984); and Sevenhuijsen, P. J., "The Photonical, Pure Grid Method", Optics and Lasers in Engineering, Vol. 18, pp. 173-194, (1993).

Digital image correlation methods are described in Peters, W. H., Ranson, W. F., "Digital imaging techniques in experimental stress analysis", Opt. Eng. Vol. 21, pp. 427-432, (1982); Bruck, H. A., McNeil, S. R., Sutton, M. A., and Peters W. H., "Digital image correlation using Newton-Raphson method of partial differential correction", Expt. Mech. Vol. 28, pp. 261-267 (1989); and Cheng, P., Sutton, M. A., Schreier, H. W., McNeill, S. R., "Full-field speckle pattern image correlation with B-Spline deformation function", Expt. Mech., Vol. 42, pp. 344-352, (2002).

The performance of methods based on digital image correlation, which rely on an applied speckle pattern, can be highly sensitive to the application method and specimen surface. Schreier, H. W. Sutton, M. A., "Systematic errors in digital image correlation due to undermatched subset shape functions", Expt. Mech., Vol. 42, pp. 303-310, (2002) discusses the sensitivity of the method to very specific qualitative and quantitative characteristics of the speckle pattern.

Additional grid-based methods are described in Sirkis, J. S., "System response to automated grid methods", Opt. Eng., Vol. 29, 1485-93, (1990) and Andersen, K., Helsch, R., "Calculation of grating coordinates using correlation filter techniques", Optik, Vol. 80, pp. 76-79, (1988). U.S. Pat. No. 7,377,181 to Christ, Jr., et al. discloses the use of coded marks.

Bremand, F. and Lagarde, A., "Two methods of large and small strain measurement on a small size area", Proc. SEM Spring Conf. On Expt. Mechanics, Keystone, Colo., USA, pp. 173-176, (1986) discloses a method of applying a Fourier transform of the grid pattern.

Mesh-free methods are described in Andrianopoulos, N. P., "Full-field displacement measurement of a speckle grid by using a mesh-free deformation function", Strain, Vol. 42, 265-271, (2006), in Andrianopoulos, N. P. and Iliopoulos, A. P. "Displacements Measurement in Irregularly Bounded Plates Using Mesh Free Methods", 16th European Conference of Fracture, Alexandroupolis, Greece, Jul. 3-7, 2006.

Two dimensional random-grid mesh-free techniques are disclosed in Andrianopoulos, N. P. and Iliopoulos, A. P., "Strain measurements by a hybrid experimental-numerical method using a mesh-free field function", Honorary Volume for Professor P. S. Theocaris, Armenian Academy of Sciences, 31-41, (2005) and in Iliopoulos, A. P., Andrianopoulos, N. P., "An Approach to Analyze Errors Introduced in the Random Grid Strain Measurement Method", Strain, Vol. 46, pp. 258-266, June 2010 (published online November 2008), and in copending patent application Ser. No. 12/793,594 to Michopoulos et al., published as U.S. Patent Publication No. 20100310128, the entire disclosure of which is incorporated herein by reference.

Three dimensional random-grid mesh-free techniques that exploit differentiations of the displacement fields are disclosed in copending patent application Ser. No. 13/565,698 to Michopoulos, et al., published as U.S. Patent Publication No. 20130063570, the entire disclosure of which is incorporated herein by reference.

Calculation of strain by differentiation of displacement fields is a typical practice in full field measurement methods. In addition, there are techniques, such as Shearography and Moiré interferometry that exploit implicit differentiations of the displacement fields, but compute only a subset of the strain components, require specialized instrumentation, are impractical for non-planar cases, and are sensitive to out of plane motions.

Strain field estimation based on differentiation of displacement fields utilized by these techniques implies that the strain compatibility equations remain satisfied for the entire domain of observation over the entire loading history, such as the continuum hypothesis remains valid. However, when surface discontinuities or strain localization occur due to damage initiation, the continuum hypothesis is no longer valid throughout the entire field of observation. Therefore, full field measurement results based on the anticipated validity of the continuous hypothesis yield both inaccurate and indeterminate measurements, thus leading to false qualitative and quantitative conclusions.

Experience with the utilization of high throughput multi-degree of freedom automated mechatronic testing machines (i.e., which are capable of loading specimens multiaxially in conjunction with energy-based inverse constitutive characterization methodologies for composite materials) has underlined the need for both automated full field data processing and an accurate encapsulation of deformation fields. Such concerns become increasingly more important in regions of a specimen that are close to, or have undergone failure and accordingly the medium can no longer be considered as a continuum. In these areas, the micro-cracks and cracks break the validity of the continuum hypothesis and the associated strain compatibility relations.

Another important issue arising from the derivation of strain from a full field displacement representation is that of relative lower accuracy near and on the boundaries of the implemented analytical representation. As the strain components are defined in terms of the derivatives of the displacement components, it is expected that the analytical approximation of the strain components will be somewhat problematic, as the displacement approximation does not impose spatially driven constraints on the formulation of its derivatives. Although it is possible to reformulate the Mesh-Free approximation of the displacement fields to take into consideration such information, this would be impractical and would require considerable and customized effort to manually guide the approximation from an algorithmic perspective in a manner that is aware of the boundaries and it remains general without need for customization from geometry to geometry.

A final issue of concern arises from the fact that if there is noise in the displacement fields, their differentiation will only amplify it for the evaluation of the strain fields.

Accordingly, there is a need for a system and method for calculating the full field of strain quantities from full field digital images of deforming specimens that addresses these and other issues. The numerical and analytical method of the present invention succeeds in approximating the strain tensor field directly from directional engineering strain quantities without requiring or enforcing the satisfaction of the compatibility conditions.

Since the present invention introduces Direct Strain Imaging (DST) as a new full field measurement method, the steps involved with the implementation of the traditional Mesh-less Random Grid (MRG) method will first be described. This will help delineate the differences and provide the basis of performance comparison between MRG and DSI methods.

Heretofore, a conventional experimental procedure for measuring a full field of deformation quantities (i.e., according to most full field methods in general, and MRG method in particular), can be outlined as follows:

1. A specimen is marked with an appropriate visible pattern that consists of a random distribution of dots distinguishable from the background.
2. If the experiment is to take into consideration out of plane motion, two or more cameras are used so that the deformation is stereoscopically reconstructed. The projective characteristics of the cameras are identified through an appropriate calibration procedure.
3. The specimen is placed in the mechanical testing machine and one image per camera is captured in the un-deformed configuration prior to the initiation of the loading sequence.
4. While the experiment is taking place, successive images of the deforming specimen are captured.
5. The images are processed and for each frame, the coordinates of appropriate points (nodes) are calculated. Those nodes may be for example geometric centroids of dots (for the case of grid methods), appropriate boundaries of geometric entities, correlated sub regions (for the case of DIC), or other such features, etc.
6. Using an interpolation or approximation scheme, a representation of the displacement field is obtained. In the MRG method, the field is represented by a continuous mesh-less approximation.
7. The strain at any point in the domain is obtained by differentiation of the displacement fields based on the definition of the strain measure as a function of the displacements.

Noise introduced by various sources is the most dominant source of error, which plagues all conventional full field measurement methods. In its presence, the MRG method has been shown to perform very well compared to other methods. The main reason for its improved performance is that the approximation scheme of the mesh-less representation works as a filter that deals well with image acquisition noise. Unfortunately, since not all noise can be removed, there is still room for improving the accuracy levels of full-field techniques. The method proposed on the present approach mitigates most of the issues described in this section.

SUMMARY

A computer-implemented method is disclosed for measuring or determining strain characteristics in a vicinity of a point of interest $w=\{x_w, y_w\}^T$ in two parametric dimensions embedded in a two or three dimensional space of a deformable domain or specimen upon which a pattern of features may be present or has been applied. The method includes (a) receiving a first image of a plurality of features of the domain or specimen, with the features capable of being represented by a plurality of nodes represented by indexes i or j in the domain in an un-deformed configuration, including representing the features as such nodes; (b) receiving a second image of the plurality of features represented by nodes represented by indexes i or j in the domain in a deformed configuration; (c) measuring engineering strains $e_{i,j}$ between a plurality of node combinations in the vicinity of w to produce $e_w = \{e_{21}, e_{31}, \ldots e_{42} \ldots, e_{n(n-1)}\}^T$; and (d) approximating strain by application of an approximation or interpolation, such as spatial moving least squares, to the engineering strains. This may be expressed by $$\left. \begin{array}{l} \varepsilon_{xx}^h(w) \equiv \varepsilon_{xx}^h(w; w) = \Phi_{xx}(w)e_w \\ \varepsilon_{yy}^h(w) \equiv \varepsilon_{yy}^h(w; w) = \Phi_{yy}(w)e_w \\ \varepsilon_{xy}^h(w) \equiv \varepsilon_{xy}^h(w; w) = \Phi_{xy}(w)e_w \end{array} \right\}$$

where $\Phi_\alpha(w) = p^T(w)M_\alpha(w)$ are shape functions of strain components for the vicinity of w for $\alpha = xx, yy, xy$. The method may involve an approximation that is a determined system or an overdetermined system.

The method can also include identifying real mean strain $e_{i,j}$ between a number of node combinations by, $$e_{i,j} = \overline{\varepsilon_{xx'}}(x_i, x_j) = \left|\frac{x'_i - x'_j}{x_i - x_j}\right| - 1, i = 1 \ldots n-1, j = 2 \ldots n, i > j,$$

where n is the number of nodes, $x_i$, $x_j$ are vectors representing a position of nodes i,j at the un-deformed configuration and $x'_i$, $x'_j$ are the same vectors in the deformed configuration.

The first and second images can be digital images. The first and second images can include a first and second sequence of images from at least two digital imaging devices positioned facing the specimen features. The method can include digitally photographing a deformable body during deformation with two or more cameras. Alternatively, other imaging system may be used, such as ultrasonography or X-ray tomography imaging. The node pattern can be identified from a visible pattern of dots or other features or markings that can be represented as nodes. The method can include determining the nodes by determining the centroid of dots or markings. The method can include identifying the plurality of nodes or node combinations via one or more image processing steps. The image processing steps can include performing light intensity integration of features of the images. The image processing step can include eliminating irregular objects from said first and second images based on the objects having an intensity below a threshold value of intensity, a pixel area outside a predetermined range, an out-of-range aspect ratio, an out-of-range moment of inertia, an out-of-range major axes direction, or an out-of-range compactness ratio.

A system for measuring strain characteristics in a vicinity of a point of interest $w=\{x_w, y_w\}^T$ in two parametric dimensions embedded in a two or three dimensional space of a deformable domain upon which a visible node pattern has been applied is disclosed. The system includes, at least two imaging devices arranged facing the pattern of nodes at different angles to the surface of the deformable body for acquiring a first image of a plurality of nodes represented by indexes i or j in the domain in an un-deformed configuration and a second image of the plurality of nodes represented by indexes i or j in the domain in a deformed configuration; and a computer processor having programmed instructions thereon for (i) measuring engineering strains between a number of node combinations in the vicinity of w to produce $e_w=\{e_{21}, e_{31}, \ldots e_{42}, \ldots, e_{n(n-1)}\}^T$; and (ii) approximating strain using a spatial moving least squares approximation. The approximation may express strain by:

$$\left.\begin{array}{l}\varepsilon^h_{xx}(w) \equiv \varepsilon^h_{xx}(w; w) = \Phi_{xx}(w)e_w \\ \varepsilon^h_{yy}(w) \equiv \varepsilon^h_{yy}(w; w) = \Phi_{yy}(w)e_w \\ \varepsilon^h_{xy}(w) \equiv \varepsilon^h_{xy}(w; w) = \Phi_{xy}(w)e_w\end{array}\right\}$$

where $\Phi_\alpha(w)=p^T(w)M_\alpha(w)$ are shape functions of strain components for the vicinity of w for $\alpha$=xx, yy, xy.

The system can also include the processor having further instructions for corresponding nodes in an un-deformed configuration with nodes in a deformed configuration, to form the plurality of node combinations, such that where $x_i$, $x_j$ are vectors representing a position of nodes i,j at the un-deformed configuration and $x'_i$, $x'_j$ are the same vectors in the deformed configuration.

The system can also include the processor having further instructions for identifying real mean strain $e_{i,j}$ between a number of node combinations by;

$$e_{i,j} = \overline{\varepsilon_{xx'}}(x_i, x_j) = \left|\frac{x'_i - x'_j}{x_i - x_j}\right| - 1, i = 1 \ldots n-1, j = 2 \ldots n, i > j.$$

The system can also include a display connected to the processor, and the processor can include instructions for displaying and storing the first and second images and a graphical representation of strain in the domain.

A computer-implemented method for measuring strain characteristics in a vicinity of a point of interest $w=\{x_w, y_w\}^T$ in two parametric dimensions embedded in a two or three dimensional space of a deformable domain upon which a node pattern has been applied is disclosed. The method includes: (a) receiving separation data for a plurality of nodes represented by indexes i or j in the domain in an un-deformed configuration; (b) receiving a separation data for the plurality of nodes represented by indexes i on in the domain in a deformed configuration; (c) measuring elongations $e_{i,j}$ between a number of node combinations in the vicinity of w to produce $e_w=\{e_{21}, e_{31}, \ldots e_{42}, \ldots, e_{n(n-1)}\}^T$; and (d) approximating strain by $$\left.\begin{array}{l}\varepsilon^h_{xx}(w) \equiv \varepsilon^h_{xx}(w; w) = \Phi_{xx}(w)e_w \\ \varepsilon^h_{yy}(w) \equiv \varepsilon^h_{yy}(w; w) = \Phi_{yy}(w)e_w \\ \varepsilon^h_{xy}(w) \equiv \varepsilon^h_{xy}(w; w) = \Phi_{xy}(w)e_w\end{array}\right\}$$

where $\Phi_\alpha(w)=p^T(w)M_\alpha(w)$ are shape functions of strain components for the vicinity of w for $\alpha$=xx, yy, xy.

The method can also include identifying real mean strain $e_{i,j}$ between a number of node combinations by;

$$e_{ij} = \overline{\varepsilon_{xx'}}(x_i, x_j) = \frac{l'_{ij} - l_{ij}}{l_{ij}} = \frac{l'_{ij}}{l_{ij}} - 1 = \left|\frac{x'_i - x'_j}{x_i - x_j}\right| - 1,$$
$$j = 1 \ldots n-1, i = 2 \ldots n, i > j$$

where $x_i$, $x_j$ are vectors representing a position of nodes ij at the un-deformed configuration and $x'_i$, $x'_j$ are the same vectors in the deformed configuration.

The method can also include deriving the separation data from neighboring markers using ultrasound or X-ray tomography.

BRIEF DESCRIPTION OF THE DRAWINGS

FIG. 4 shows a table of integral basis monomials.

DESCRIPTION

The present method and system involves or enables the analysis of full-field spatial distributions of strain tensor field components in a two or three-dimensional space, as a consequence of deformation under generalized loading conditions, even when such deformation creates discontinuities. An aspect of the present approach is that it does not require the determination or use of displacement vector distribution. In other words, strain tensor fields are 'directly' calculated as a tensor approximation from the engineering strain within the space or domain of interest.

Figure 1:
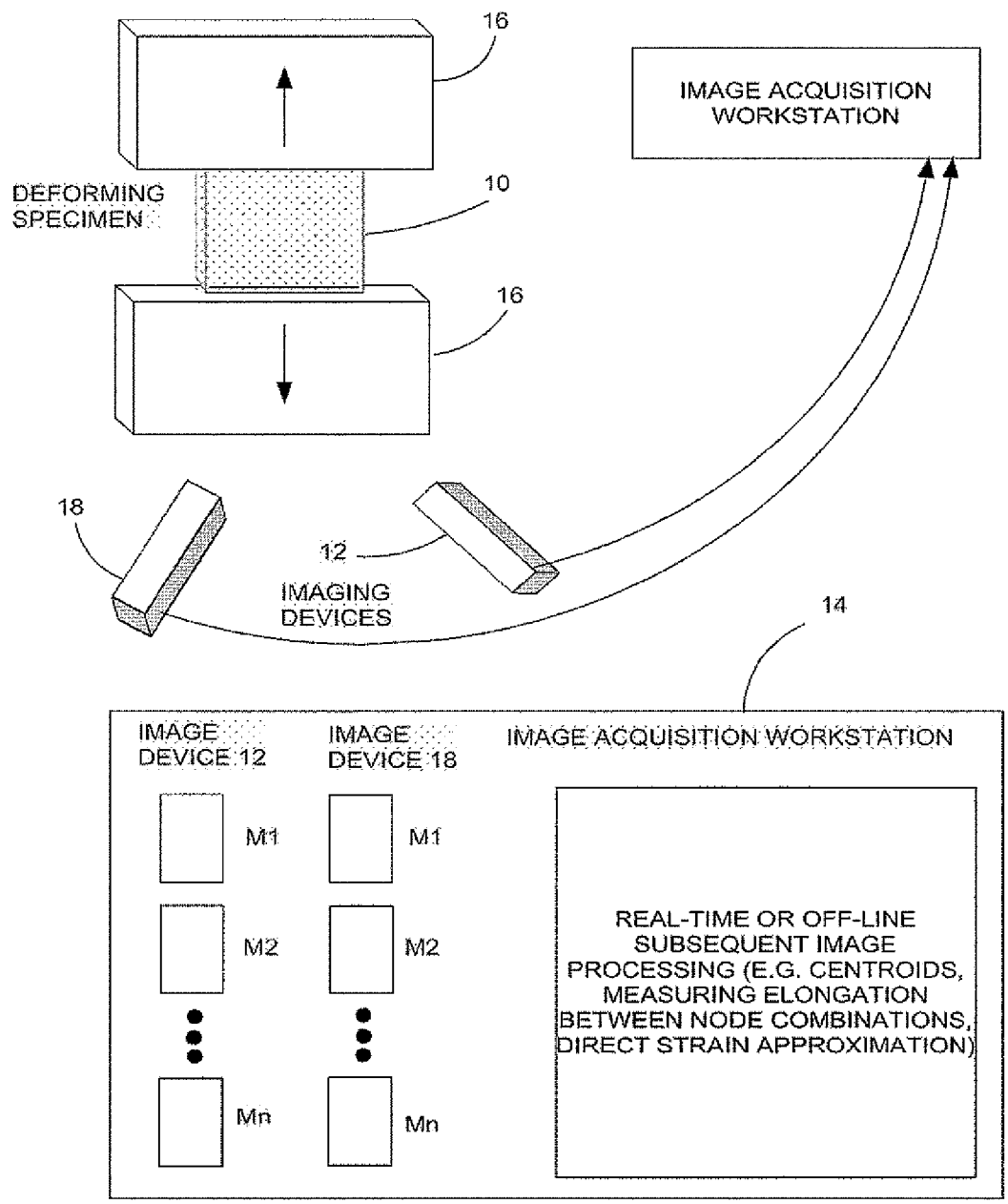
FIG. 1 shows a system for measuring deformation of a surface in three dimensions, including two video cameras, a materials testing machine and specimen, and an image acquisition workstation.

FIG. 1 shows an embodiment of the system or basic instrumentation that can be used for measuring deformation of a surface or domain in three dimensions, including a stereoscopic embodiment with two digital imaging devices, such as video cameras 12 and 18, capturing images of a deforming specimen 10, a materials testing machine 16, and an image acquisition workstation 14.

By capturing images of deforming specimen 10, digital imaging devices 12, 18 may capture a first and second image with a first image in an un-deformed configuration and a second image in a deformed configuration. In some applications, first and second images may comprise a sequence of images from the at least two digital imaging devices 12, 18.

The method can include generating and applying a pattern of marks to the specimen to be deformed. The pattern can be a random pattern. The marks applied to the specimen can be any color that is optically distinguishable from the surface of the body. This distinguishability does not necessarily need to appear at the human visible light wavelength, but can be at any range that an appropriate camera can image. This range can be, but is not limited to, the infrared range, the ultraviolet range, the radar range, the X-ray range, or the gamma ray range. The marks or spots can be of various shapes and sizes, including round dots, squares, ellipses, lines, or random patterns generated by a computer or printer. The marks or spots can be applied by printing ink directly on the specimen, by manually applying printed dots with adhesive, or randomly sprayed onto the specimen. In addition, some subjects have a surface that contains spots that can be regarded as dots, so it is not necessary to apply any additional markings. For very large structures evaluated outside the laboratory, such as a portion of a bridge, the dots can be applied with paint.

In an exemplary embodiment, the marks are round black ink dots printed on a generally-planar surface of a specimen to be deformed. A characteristic point or "node" for each of the marks is determined. The characteristic point can be centroids of regions in close proximity that share light intensity and/or color characteristics. Preferably, the characteristic point is a geometric point that is mostly invariable relative to the overall position of the dot. Those invariable points may be the light intensity centroids of connected components (dots), the two edges of a line, or characteristic points of a pattern such as the center of a circle or the two foci of an ellipse. In addition, or as an alternative, to deliberately-applied markings, other suitable features of the specimen or subject may be represented as nodes for use with the present method.

Generally, a "node" refers to the geometric point, i.e. an infinitesimal quantity describing spatial coordinates. The features of a specimen domain or surface of interest have a certain non-infinitesimal (i.e. measurable) size. However, for every feature within an image, one may identify a characteristic point (i.e. a node) which is usually the geometric centroid of the respective feature. Such a feature may be a dot based on light intensity profile. A point for such a feature may be identified by integrating (i e summing) the light intensity moments over x and y and dividing by the total volume (i.e. the sum of the light intensities shown in the images).

Figure 2:
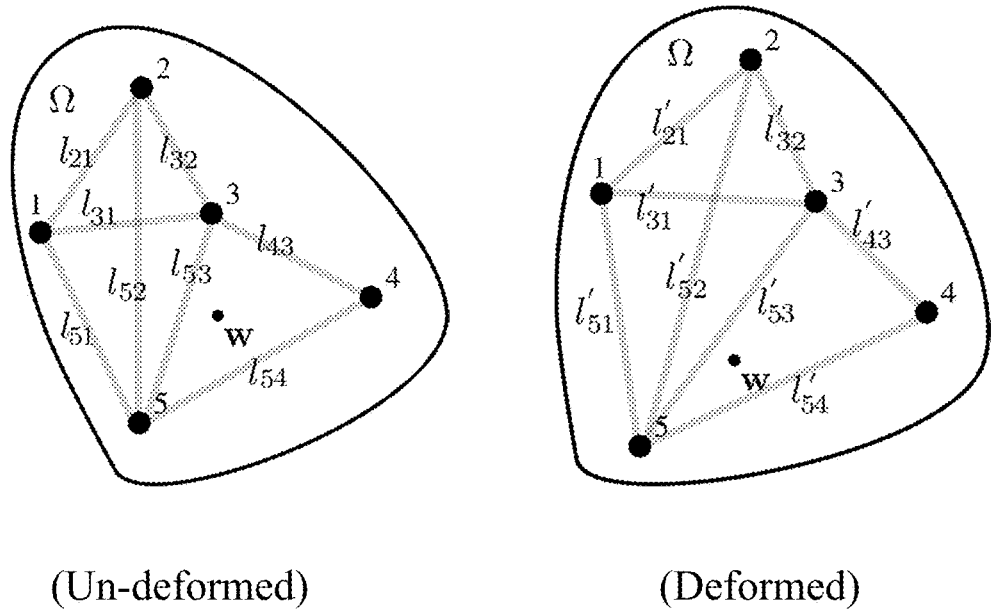
FIG. 2 shows the deformation configurations and distances of selected node pairs of a domain $\Omega$.

The engineering strain between pairs of adjacent nodes along the directions defined by the pair, may be digitally determined from data input for the proposed analysis. A domain Ω in the un-deformed and deformed configuration is shown in FIG. 2, populated with a number of such nodes. For a set of n nodes in the vicinity of an interest point described by a position vector $w=\{x_w, y_w\}^T$, it is possible to form a number of engineering strain quantities $e_{ij}=(l'_{ij}-l_{ij})/l_{ij}$, i=1 . . . n−1, j=2 . . . n, i<j in terms of the distances $l_{ij}$, $l'_{ij}$ in the initial or un-deformed and deformed configurations, respectively. Each of those quantities may be considered as the average of the strain component in the direction of the line connecting the two nodes over the respective line segment. Given those engineering strains and the coordinates of the nodes, one may seek to calculate the strain tensor at any point w in the domain. It is important to note that similar to traditional meshless methods, the vicinity of a point of interest $w=\{x_w, y_w\}^T$ is bound by an appropriate Domain Of Support (DOS), which can be taken to be circular, for example.

The solution of this problem might be at first considered as the extension of the typical 3 gauge rosette strain calculation. However, this would only hold true if the strain field is considered constant throughout the region of interest. In calculating the strain from a strain rosette, it is generally assumed that the engineering strains measured by each directional strain gauge of the rosette, all occur at the same point. Although this might be true for certain strain gauge rosette configurations, it is certainly not the case under the requirements of the present problem, because the engineering strain quantities cannot be considered as having been measured at the same point.

It should be noted that although the present method and system are used in the context of full field strain measurements using digital imaging information in the visual spectrum, it can be also applied to any other spectrum or context where appropriate data can be acquired. For example, engineering strain data may be obtained by quantifying separation distances between neighboring markers via the use of ultrasound or x-ray tomography techniques and the respective full field strain tensor could be calculated between appropriate volumetric speckles by the method discussed herein. The same is true for all methods that can identify marker separation on surfaces of deformable bodies. Thus, it is contemplated that the present approach may provide useful application in diagnostic methods in healthcare, among others. Further, the term domain should be construed as a portion or all of a body and being applicable to a variety of materials, whether metallic structures or tissue of an animal or human subject.

In the following section, a solution to this problem is presented by the means of a spatial moving least squares approximation. The inventors have discovered that the step of applying this approximation to engineering strains between a plurality of node combinations obtains a high level of performance in determining or measuring strain without the prior vulnerability to noise.

An aspect is to identify the strain tensor components at any point described by a position vector $w=\{x_w, y_w\}^T$ within a deformable domain (i.e., with $\epsilon^h$ designating approximate or hypothetical strain). An approximation of the components of the 2-dimensional strain tensor at any point $x=\{x, y\}^T$ in the vicinity of w, may be expressed by, $$\left.\begin{aligned}\varepsilon_{xx}^h(w; x) &= \sum_{j}^{m} p_j(x)a_j^{xx}(w) = p^T(x)a^{xx}(w) \\ \varepsilon_{yy}^h(w; x) &= \sum_{j}^{m} p_j(x)a_j^{yy}(w) = p^T(x)a^{yy}(w) \\ \varepsilon_{xy}^h(w; x) &= \sum_{j}^{m} p_j(x)a_j^{xy}(w) = p^T(x)a^{xy}(w)\end{aligned}\right\} \quad (1)$$

where p(x) is a vector of basis functions that can be chosen to consist of m monomials of the lowest orders to ensure minimum completeness. A polynomial basis of order M<m has the general form, $$p(x)=p(x,y)=\{1,x,y,xy,x^2,y^2,\ldots,x^M,y^M\}^T. \quad (2)$$

Such a polynomial basis can be constructed by concatenation of the complete order terms using the Pascal triangle of monomials. It should be noted that the polynomial basis could be chosen to be different for each of the strain components, but this would introduce algebraic complexity that is not presently justified. In addition, $a^\alpha(w)$, $\alpha=xx, yy, xy$ are vectors of coefficients specific to every point w of the domain:

$$a^\alpha(w)=\{a_0^\alpha, a_1^\alpha, \ldots, a_m^\alpha\}^T, \alpha=xx,yy,xy. \quad (3)$$

In contrast to the MRG method, the present method and system seek to directly calculate the strain components. Therefore, it is first necessary to identify the engineering strains between a number of node combinations.

The normal strain at an angle θ relative to a global coordinate system may be given by the transformation, $$\varepsilon_{xx'} = \frac{\varepsilon_{xx} + \varepsilon_{yy}}{2} + \frac{\varepsilon_{xx} - \varepsilon_{yy}}{2}\cos 2\theta + \varepsilon_{xy}\sin 2\theta. \quad (4)$$

Using Eqns. (4) and (1), one can derive the function that approximates the xx strain tensor component at a point $x=\{x, y\}^T$ on a coordinate system Ax'y' forming an angle θ with the global coordinate system Axy (FIG. 3) in the vicinity of w, as follows, $$\varepsilon_{xx'}^h(w; x) = \frac{p^T(x)a^{xx}(w) + p^T(x)a^{yy}(w)}{2} + \quad (5)$$
$$\frac{p^T(x)a^{xx}(w) - p^T(x)a^{yy}(w)}{2}\cos 2\theta + p^T(x)a^{xy}(w)\sin 2\theta,$$

or:

$$\varepsilon_{xx'}^h(w; x) = p^T(x)a^{xx}(w)\cos^2\theta + p^T(x)a^{yy}(w)\sin^2\theta + p^T(x)a^{xy}(w)\sin 2\theta. \quad (6)$$

Figure 3:
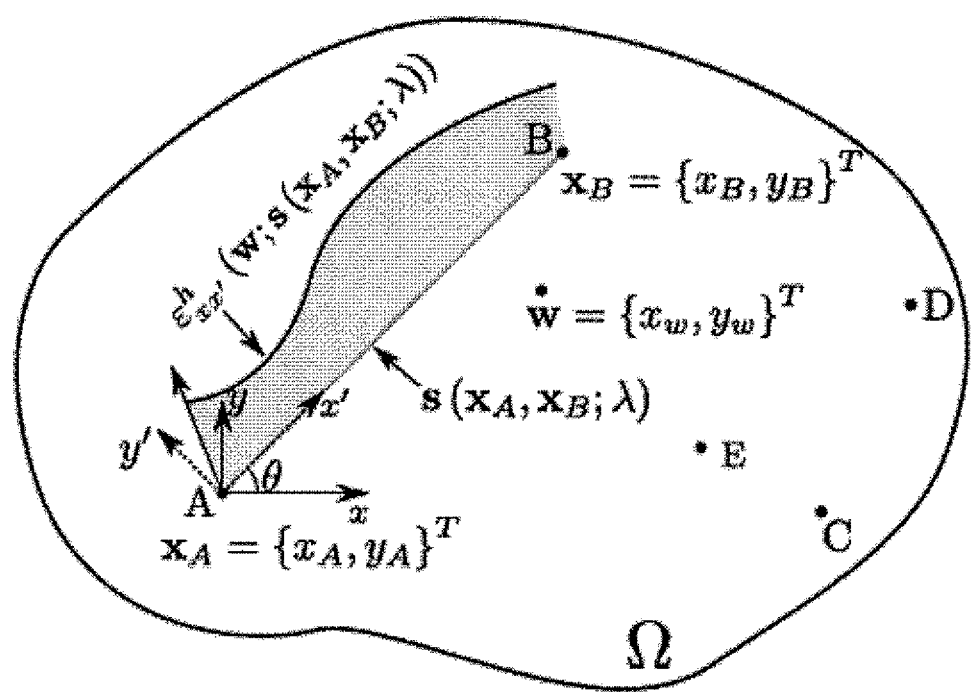
FIG. 3 shows strain component $\varepsilon_{xx'}^h$ of the approximation in the direction of AB relative to the local coordinate system at point A.

FIG. 3 shows strain component $\epsilon_{xx'}^h$ of the approximation in the direction of AB relative to the local coordinate system at point A. Within the domain Ω (FIG. 3) and in the vicinity of a point expressed by the vector w, assume the existence of two neighbouring nodes A and B expressed by the vectors $x_A=\{x_A, y_A\}^T$ and $x_B=\{x_B, y_B\}^T$ respectively. The mean strain between these two nodes as derived by Eqn. (6) can be defined by, $$\overline{\varepsilon_{xx'}^h}(w; x_A, x_B) = \frac{\int_0^1 \varepsilon_{xx'}^h(w; s(x_A, x_B; \lambda))\left|\frac{\partial s(x_A, x_B; \lambda)}{\partial \lambda}\right|d\lambda}{|x_B - x_A|}, \quad (7)$$

where $s(x_A, x_B; \lambda)$ is the parametric expression of the line segment passing from both A and B, and is given by:

$$s(x_A,x_B;\lambda)=(1-\lambda)x_A+\lambda x_B==\{(1-\lambda)x_A+\lambda x_B,(1-\lambda)y_A+\lambda y_B\}, \lambda\in[0,1]. \quad (8)$$

One may prove that, $$\left|\frac{\partial s(x_A, x_B; \lambda)}{\partial \lambda}\right| = |x_B - x_A| \quad (9)$$

and hence Eqn. (7) simplifies to:

$$\overline{\varepsilon_{xx'}^h}(w; x_A, x_B) = \int_0^1 \varepsilon_{xx'}^h(w; s(x_A, x_B; \lambda))d\lambda. \quad (10)$$

The line integral in Eqn. (10) can then be derived by combining Eqns. (6), and (8), $$\int_0^1 \varepsilon_{xx'}^h(w; s(x_A, x_B; \lambda))d\lambda = \quad (11)$$
$$\int_0^1 [p^T(s)a^{xx}(w)\cos^2\theta + p^T(s)a^{yy}(w)\sin^2\theta + p^T(s)a^{xy}(w)\sin 2\theta]d\lambda.$$

The angle θ can be calculated by the non-ambiguous arctangent of the vector $x_B$-$x_A$. Splitting up the integral and distributing the independent terms outside the integrands yields, $$\int_0^1 \varepsilon_{xx'}^h(w; s(x_A, x_B; \lambda))d\lambda = \left[\cos^2\theta \int_0^1 p^T(s(x_A, x_B; \lambda))d\lambda\right]a^{xx}(w) + \quad (12)$$
$$\left[\sin^2\theta \int_0^1 p^T(s(x_A, x_B; \lambda))d\lambda\right]a^{yy}(w) +$$
$$\left[\sin 2\theta \int_0^1 p^T(s(x_A, x_B; \lambda))d\lambda\right]a^{xy}(w).$$

The vector integrals in Eqn. (12) may be calculated for a given polynomial basis, and can be derived from the terms of FIG. 4. If a full order polynomial is chosen, the integral basis vector can be constructed by concatenation of the respective terms. For example if a 6 term basis vector is chosen to be $p(x)=p(x, y)=\{1, x, y, xy, x^2, y^2\}^T$, the integral basis vector will be, $$r^T(x_A, x_B) = \int_0^1 p^T(s(x_A, x_B; \lambda))d\lambda = \quad (13)$$
$$\left\{1, \frac{1}{2}(x_A + x_B), \frac{1}{2}(y_A + y_B), \frac{1}{6}(x_A(2y_A + y_B) + x_B(y_A + 2y_B)),\right.$$

-continued $$\frac{1}{3}(x_A^2 + x_A x_B + x_B^2), \frac{1}{3}(y_A^2 + y_A y_B + y_B^2)\Big\}.$$

The choice of an appropriate polynomial basis will yield an integral vector basis $r^T(x_A, x_B)$. Thus, Eqn. (12) can be written, $$\int_0^1 \varepsilon_{xx'}^h(w; s(x_A, x_B; \lambda)) = [r^T(x_A, x_B)\cos^2\theta] a^{xx}(w) + \quad (14)$$
$$[r^T(x_A, x_B)\sin^2\theta] a^{yy}(w) + [r^T(x_A, x_B)\sin 2\theta] a^{xy}(w),$$

or, $$\int_0^1 \varepsilon_{xx'}^h(w; s(x_A, x_B; \lambda)) d\lambda = \quad (15)$$
$$q_{xx}^T(x_A, x_B) a^{xx}(w) + q_{yy}^T(x_A, x_B) a^{yy}(w) + q_{xy}^T(x_A, x_B) a^{xy}(w),$$

with $$\left.\begin{array}{l} q_{xx}^T(x_A, x_B) = r^T(x_A, x_B)\cos^2\theta \\ q_{yy}^T(x_A, x_B) = r^T(x_A, x_B)\sin^2\theta \\ q_{xy}^T(x_A, x_B) = r^T(x_A, x_B)\sin 2\theta \end{array}\right\}. \quad (16)$$

Collecting the terms of Eqn. (15) into larger vectors, and substituting in (7) yields, $$\overline{\varepsilon_{xx'}^h}(w; x_A, x_B) = q^T(x_A, x_B) a(w), \quad (17)$$

with, $$\left.\begin{array}{l} q^T(x_A, x_B) = \{q_k^{AB}\} = \\ \{q_{xx}^T(x_A, x_B), q_{yy}^T(x_A, x_B), q_{xy}^T(x_A, x_B)\} \\ a(w) = \{a_k\} = \{(a^{xx}(w))^T, (a^{yy}(w))^T, (a^{xy}(w))^T\}^T \\ k = 1 \ldots 3m \end{array}\right\}. \quad (18)$$

Eqn. (17) describes the approximated mean strain between any two nodes in the domain at the vicinity of point w. When the coordinates of the nodes are determined using a digital imaging technique, it is possible to calculate the real mean strain (aka the engineering strain) between any two of the n nodes as, $$e_{ij} = \overline{\varepsilon_{xx'}}(x_i, x_j) = \frac{l'_{ij} - l_{ij}}{l_{ij}} = \frac{l'_{ij}}{l_{ij}} - 1 = \frac{|x'_i - x'_j|}{|x_i - x_j|} - 1, \quad (19)$$
$$j = 1 \ldots n-1, i = 2 \ldots n, i < j$$

where $x_i$, $x_j$ are the vectors representing the positions of nodes i, j at the un-deformed configuration and $x_i'$, $x_j'$ are the same vectors in the deformed configuration. The scalar quantities $e_{ij}$ should not be thought of as the elements of a matrix, but rather as a set of $n(n-1)/2$ numbers. Although, not of interest in the current analysis, the latter can be thought as functions of $x_i$, $x_j$ and time. The condition expressing that i should be less than j ensures the requirement that no combination is considered twice. A functional of weighted residuals can now be constructed by using Eqns. (17) and (19) as follows, $$J = \sum_{j=1, i=2, i>j}^{n-1,n} W\left(w - \frac{x_i + x_j}{2}\right)\left(\overline{\varepsilon_{xx'}^h}(w; x_i, x_j) - \overline{\varepsilon_{xx'}}(x_i, x_j)\right)^2 \quad (20)$$

$$= \sum_{j=1, i=2, i>j}^{n-1,n} W\left(w - \frac{x_i + x_j}{2}\right)(q^T(x_i, x_j) a(w) - e_{ij})^2$$

where $W(w-(x_i+x_j)/2) = W_{ij} \geq 0$ is a weight function that decreases with distance. A common weight function is the cubic spline weight function given by:

$$W(d) = W(\hat{d}) = \begin{cases} \frac{2}{3} - 4\hat{d}^2 + 4\hat{d}^3, & \hat{d} \leq \frac{1}{2} \\ \frac{4}{3} - 4\hat{d} + 4\hat{d}^2 - \frac{4}{3}\hat{d}^3, & \frac{1}{2} < \hat{d} \leq 1 \\ 0, & d > 1 \end{cases} \quad (21)$$

with $$\hat{d} = \frac{|d|}{d_w},$$

the normalized distance, and $d_w$ the smoothing length that is usually equal to the extent of the domain of support.

It should be noted that any strain component could be used in the functional of Eqn. (20) and that all of them are present in this equation because of Eqn. (4). The notation j=1, i=2, i>j represents the set of all combinations between the indexes i and j. The least-squares minimization of the residual defined by Eqn. (20) will provide the values of coefficients in the vector a(w) so that $\overline{\varepsilon_{xx'}^h}(w; x_i, x_j)$ optimally approximates $\overline{\varepsilon xx'}(x_i, x_j)$. To minimize the residual in Eqn. (20) with respect to a, form the derivatives, $$\frac{\partial J}{\partial a} = 0 \Rightarrow \frac{\partial J}{\partial a_k} = 0, k = 1 \ldots 3m \quad (22)$$

that can be expanded to:

$$\frac{\partial J}{\partial a_k} = \frac{\partial \sum_{j=1,i=2,i>j}^{n-1,n} W_{ij}\left(\sum_{r=1}^{3m} q_r^{ij} a_r - e_{ij}\right)^2}{\partial a_k} = \quad (23)$$

$$= 2\sum_{j=1,i=2,i>j}^{n-1,n} W_{ij}\left(\sum_{r=1}^{3m} q_r^{ij} a_r - e_{ij}\right)\frac{\partial\left(\sum_{r=1}^{3m} q_r^{ij} a_r - e_{ij}\right)}{\partial a_k}$$

$$= 2\sum_{j=1,i=2,i>j}^{n-1,n} W_{ij}\left(\sum_{r=1}^{3m} q_r^{ij} a_r - e_{ij}\right) q_k^{ij}$$

$$= 2\sum_{j=1,i=2,i>j}^{n-1,n} W_{ij} \sum_{r=1}^{3m} q_k^{ij} q_r^{ij} a_r - 2\sum_{i,j=1,i>j}^{n} W_{ij} q_k^{ij} e_{ij}$$

Introducing this expression to Eqn. (22) yields:

$$\sum_{j=1, i=2, i>j}^{n-1, n} \left( W_{ij} \sum_{r=1}^{3m} q_k^{ij} q_r^{ij} a_r \right) = \sum_{j=1, i=2, i>j}^{n-1, n} W_{ij} q_k^{ij} e_{ij}. \tag{24}$$

In matrix notation the last expression can be written as, $$Q(w)a(w) = B(w)e_w, \tag{25}$$

or, $$a(w) = Q^{-1}(w)B(w)e_w = M(w)e_w, \tag{26}$$

in which, $$e_w = \{e_{21}, e_{31}, e_{32}, e_{41}, e_{42}, \ldots, e_{n(n-1)}\}^T, \tag{27}$$

is a vector that collects all the measured engineering strains in the vicinity of w, B is a matrix that has the form, $$\left. \begin{array}{l} B(w) = [b_{21}, b_{31}, b_{32}, b_{41}, b_{42}, \ldots, b_{n(n-1)}] \\ b_{ij}(w) = W\left(w - \frac{x_i + x_j}{2}\right) q(x_i, x_j) \end{array} \right\}, \tag{28}$$

and Q(w) is defined by:

$$Q(w) = \sum_{j=1, i=2, i>j}^{n-1, n} W\left(w - \frac{x_i + x_j}{2}\right) q(x_i, x_j) q^T(x_i, x_j) \tag{29}$$

In order for the system of equations (25) to be fully determined, the number of equations has to be equal to 3m where m is the number of monomials in the polynomial basis. For most cases the strain values are to be acquired by all the combinations between n nodes, and therefore:

$$\frac{n(n-1)}{2} = 3m \xrightarrow{m>1} n = \frac{1}{2}\left(1 + \sqrt{1 + 24m}\right).$$

However, an overdetermined system would lead to noise reduction and thus is preferable. This may be expressed by, $$n \geq \frac{1}{2}\left(1 + \sqrt{1 + 24m}\right). \tag{30}$$

This inequality can be used in conjunction with additional considerations for the identification of the extent of the domain of support.

The matrix $M(w) = Q^{-1}(w)B(w)$ will be of size $3m \times n$ where each row corresponds to an element of the vectors described in Eqn. (3).

Partitioning this matrix vertically into 3 sub-matrices of dimensions $m \times n$ yields:

$$M(w) = \begin{bmatrix} M_{xx}(w) \\ M_{yy}(w) \\ M_{xy}(w) \end{bmatrix}. \tag{31}$$

It is now possible to express the coefficients vectors as, $$\left. \begin{array}{l} a^{xx}(w) = M_{xx}(w)e_w \\ a^{yy}(w) = M_{yy}(w)e_w \\ a^{xy}(w) = M_{xy}(w)e_w \end{array} \right\}. \tag{32}$$

Substitution of these expressions in Eqns. (1), yields the final form of the fully defined strain field approximation expressions, $$\left. \begin{array}{l} \varepsilon_{xx}^h(w) \equiv \varepsilon_{xx}^h(w; w) = \Phi_{xx}(w)e_w \\ \varepsilon_{yy}^h(w) \equiv \varepsilon_{yy}^h(w; w) = \Phi_{yy}(w)e_w \\ \varepsilon_{xy}^h(w) \equiv \varepsilon_{xy}^h(w; w) = \Phi_{xy}(w)e_w \end{array} \right\}, \tag{33}$$

where $\Phi_\alpha(w) = p^T(w)M_\alpha(w)$, are shape functions of the strain components for the point w for $\alpha = xx, yy, xy$.

A desirable property of approximations is consistency. That is to say, given a field that is expressed by a specific basis function, then it should be reproducible in an exact manner by the approximation when using this basis function.

The actual fields of the components of the strain tensor of a domain may be given by:

$$\left. \begin{array}{l} \varepsilon_{xx}(x) = \sum_j^k p_j(x)c_j^{xx}(x) \\ \varepsilon_{yy}(x) = \sum_j^k p_j(x)c_j^{yy}(x) \\ \varepsilon_{xy}(x) = \sum_j^k p_j(x)c_j^{xy}(x) \end{array} \right\}. \tag{34}$$

Assume that the same fields are to be approximated by functions of the form given by Eqns. (1) with m=k and the same basis with Eqn. (34) i.e., $$\left. \begin{array}{l} \varepsilon_{xx}^h(x) = \sum_j^k p_j(x)a_j^{xx}(x) \\ \varepsilon_{yy}^h(x) = \sum_j^k p_j(x)a_j^{yy}(x) \\ \varepsilon_{xy}^h(x) = \sum_j^k p_j(x)a_j^{xy}(x) \end{array} \right\}. \tag{35}$$

It is obvious that J in Eqn. (20) will be equal to 0 for $a_j^\alpha(w) = c_j^\alpha(x)$ and since J is positive definite this value will represent the minimum minimorum. In addition, because the sum of Eqns. (35) yields a linear combination of the coefficients, this minimum will also be unique.

Hence, replacing $a_j^\alpha$ with $c_j^\alpha$ in (35) yields, $$\epsilon_{xx}^h(x) = \epsilon_{xx}(x), \epsilon_{xx}^h(x) = \epsilon_{yy}(x), \epsilon_{xx}^h(x) = \epsilon_{xy}(x) \tag{36}$$

This demonstrates that the approximated fields of Eqn. (35) and hence Eqn. (1) reproduce exactly the fields described by Eqn. (34).

The effects of the condition number in mesh-less surface fitting are critical only in the sense of invertibility, and do not have a proven relationship with the effectiveness of the regression. Accordingly, in the case of the present method the uniqueness of the solution—as expressed by the condition number—is not of utmost importance either. However, it is worthwhile noting that the condition number should not be outrageously high in order to allow the approximation of the tensor surface from a numerical perspective. To demonstrate this point, consider that the system matrix of interest as indicated in Eqn. (25) is Q.

Figure 5:
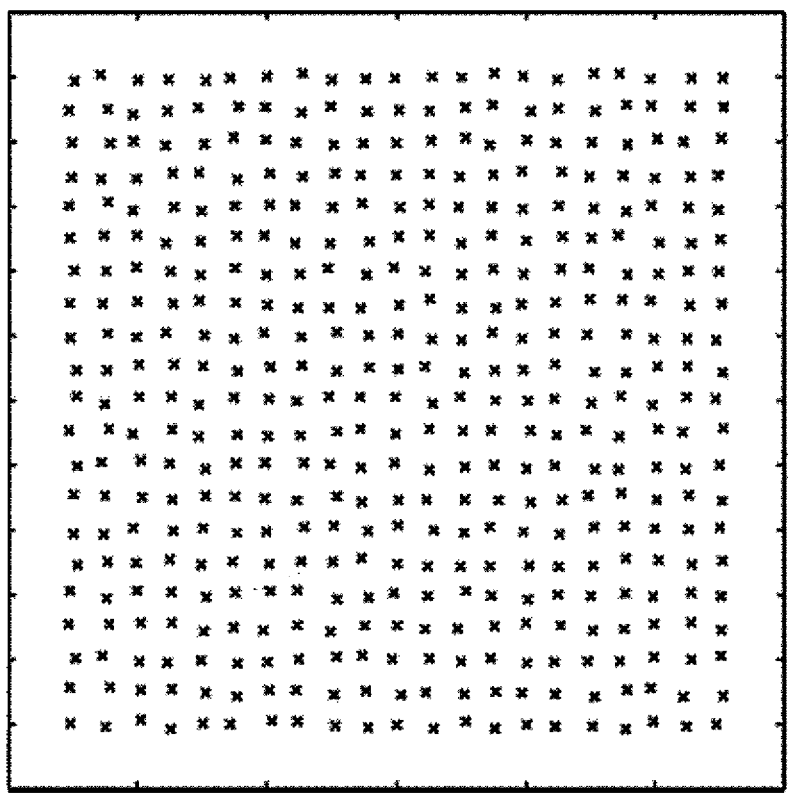
FIG. 5 shows a random distribution of nodes generated in a square domain of a unit length.

In order to study the effects of the domain of support and the number of monomial terms used in the polynomial basis a number of numerical tests were performed. A random distribution of nodes was generated in a square domain of a unit length as shown in FIG. 5. The matrix Q was calculated using Eqn. (29) for a number of domain of support radius values and for a number of monomial terms of the polynomial basis function of Eqn. (2).

Figure 6:
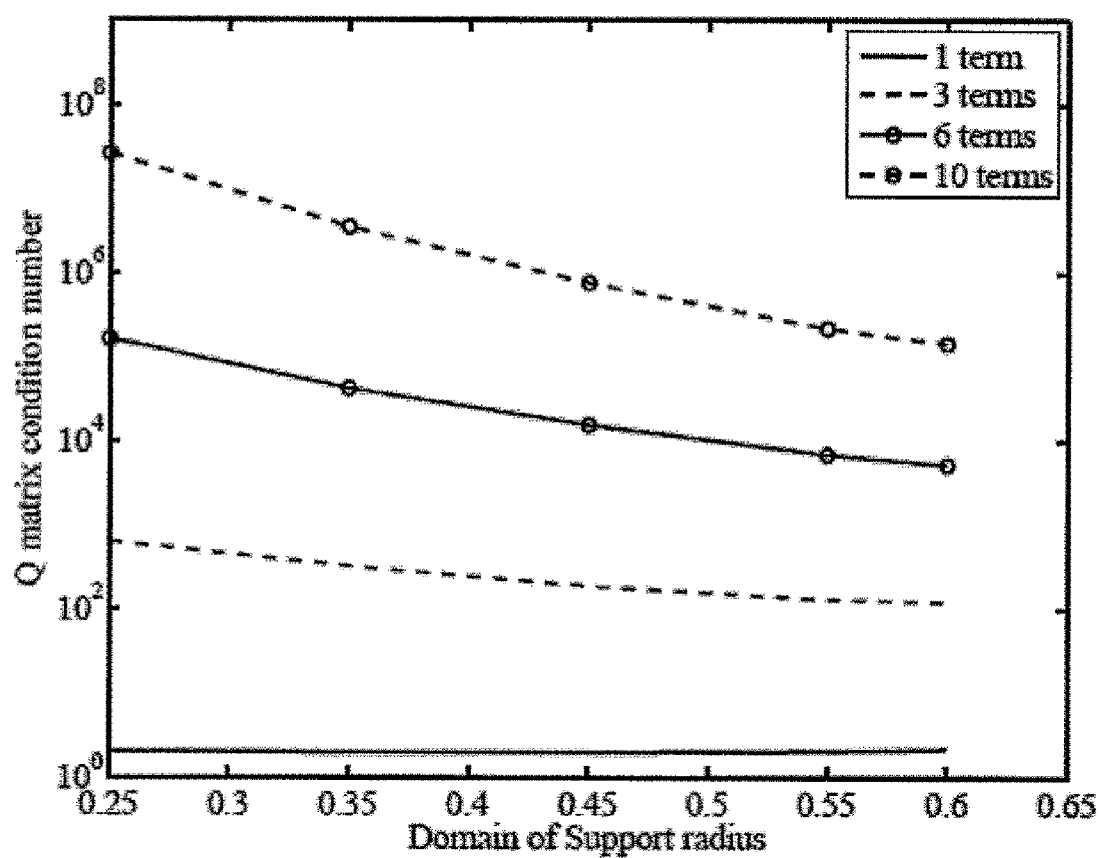
FIG. 6 is a graph plotting the condition number of matrix Q vs. radius of domain of support for polynomials with various numbers of monomial terms.

The condition number of matrix Q is plotted versus the domain of support radius in FIG. 6. In this plot it is observed that for polynomial basis with 1 and 3 terms, the condition number is very low, indicating very stable solutions. For higher number of monomial terms the respective condition numbers tends to be larger but in acceptable ranges especially when compared to other mesh-less methods.

Figure 7:
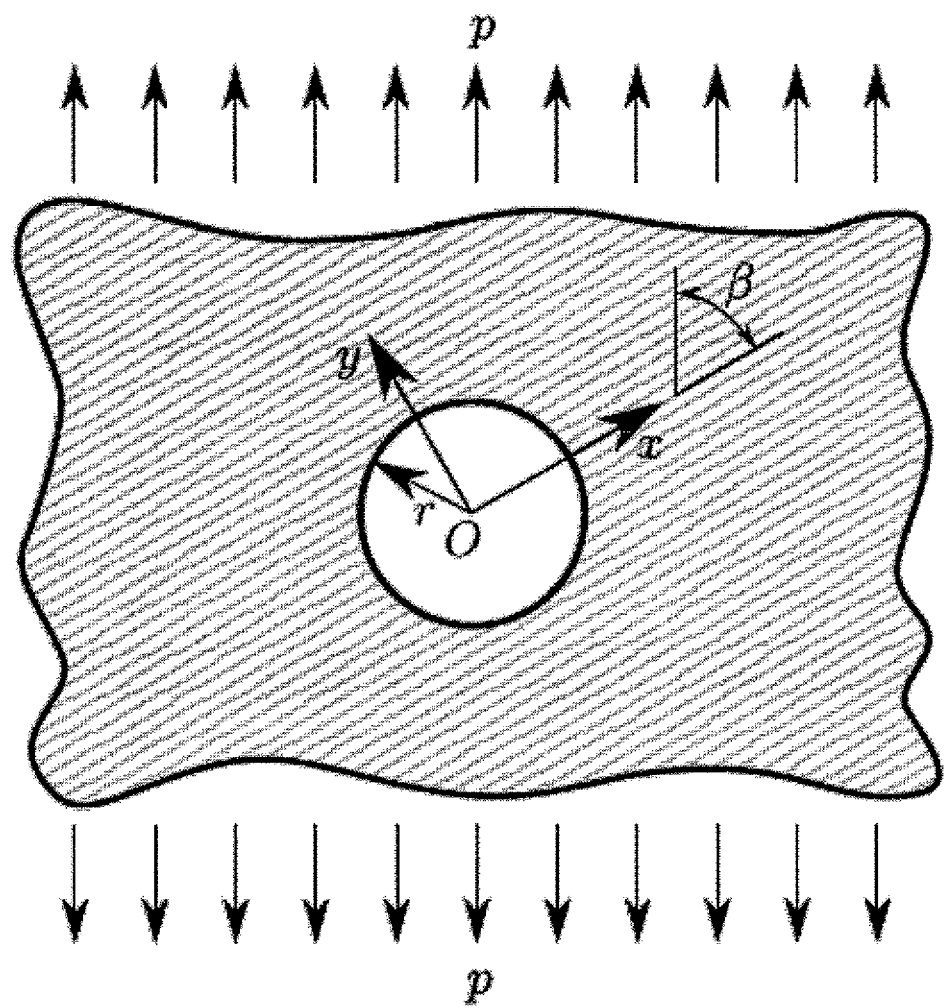
FIG. 7 shows an orthotropic infinite plate with circular hole and load at infinity.

Since present approach is a consistent approximation, it is expected that it can exactly reproduce simple polynomial fields; hence, it is more interesting to validate it in more realistic and complex situations. To this end, a set of synthetic validation experiments was conducted on a well known deformation field resulting from the tensile loading of an orthotropic body with a circular hole (FIG. 7). The direction of hatch lines coincides with the coordinate system's Ox axis and the major orthotropic direction.

In order to evaluate the performance of the present approach relative to the MRG method, synthetic experiments were developed by applying both methods, and their error relative to the known analytic solution was calculated. The error metric utilized was defined as, $$e_m^i = |\varepsilon_a^i - \varepsilon_m^i| \\ e_d^i = |\varepsilon_a^i - \varepsilon_d^i|$$ (37)

where i=1 ... N is indexing of the N evaluation points, $\varepsilon_a^i$ is the strain as calculated from the analytic solution at point i, $\varepsilon_m^i$, and $\varepsilon_d^i$ is the strain on point i from the MRG and DSI methods respectively. The mean absolute error over a set of nodes is calculated by:

$$e_m = \frac{1}{N}\sum_{i=1}^N |\varepsilon_a^i - \varepsilon_m^i| \\ e_d = \frac{1}{N}\sum_{i=1}^N |\varepsilon_a^i - \varepsilon_d^i|$$ (38)

Furthermore, since the prevailing source of errors in full field measurements is that of the noise by the imaging sensor, a simple sensitivity study was conducted for various levels of noise. To investigate the effect the actual strain field might have on both methods, the synthetic tests with varying load inclination were also conducted.

Consider an infinitely large orthotropic elastic plate that contains a circular hole of radius r that is subjected to a stress state at infinity equal to p. The applied load forms an angle β with the major orthotropic axis as shown in FIG. 7. The angle β essentially controls the degree of anisotropy introduced in the strain-stress fields and varying it amounts to rotating the major orthotropic axis relative to the loading direction (i.e. dual description of the angle). Strain at any point on the plane is expressed by the elastic constitutive equations, $$\varepsilon_{xx} = a_{11}\sigma_{xx} + a_{12}\sigma_{yy} + a_{16}\tau_{xy} \\ \varepsilon_{yy} = a_{12}\sigma_{xx} + a_{22}\sigma_{yy} + a_{26}\tau_{xy} \\ \gamma_{xy} = a_{16}\sigma_{xx} + a_{26}\sigma_{yy} + a_{66}\tau_{xy}$$ (39)

It has been shown that the composition of Eqns. (39) for the general case of multiply connected plane problems, can be reduced to a set of algebraic equations in terms of holomorphic functions expressed in the complex plane with the help of the mathematical theory of elasticity. In fact, the general solution to this problem for an elliptic hole is known and is implemented here for an ellipse of minor to major axes aspect ratio of unity, in order to reflect the problem when the hole is circular. Additional modifications have been introduced to account for rotations of the medium at infinity.

The stresses are calculated by the equations, $$\sigma_{xx} = \sigma_{xx}^\infty + 2\mathrm{Re}\left[s_1^2 \frac{\partial \phi_0(z_1)}{\partial z_1} + s_2^2 \frac{\partial \psi_0(z_2)}{\partial z_2}\right] \\ \sigma_{yy} = \sigma_{yy}^\infty + 2\mathrm{Re}\left[\frac{\partial \phi_0(z_1)}{\partial z_1} + \frac{\partial \psi_0(z_2)}{\partial z_2}\right] \\ \tau_{xy} = \tau_{xy}^\infty - 2\mathrm{Re}\left[s_1 \frac{\partial \phi_0(z_1)}{\partial z_1} + s_2 \frac{\partial \psi_0(z_2)}{\partial z_2}\right]$$ (40)

where, $s_1$, $s_2$ are the roots of, $$a_{11}s^4 - 2a_{16}s^3 + (2a_{12}+a_{66})s^2 - 2a_{26}s + a_{22} = 0.$$ (41)

It has been shown that Eqn. (41) has no real roots and is therefore always of the form, $$s_{1,3}=a_1 \pm b_1 i, s_{2,4}=a_2 \pm b_2 i, b_1 \geq 0, b_2 > 0.$$ (42)

The stress state at infinity is given by:

$$\sigma_{xx}^\infty = p\cos^2\beta, \sigma_{yy}^\infty = p\sin^2\beta, \tau_{xy}^\infty = p\cos\beta\sin\beta,$$ (43)

while the holomorphic functions are, $$\varphi_0(z_1) = -\frac{ir[\sigma_x^\infty + is_2\sigma_y^\infty + (s_2+i)\tau_{xy}^\infty]}{2(s_1-s_2)}\zeta_1(z_1) \\ \psi_0(z_2) = -\frac{ir[\sigma_x^\infty + is_1\sigma_y^\infty + (s_1+i)\tau_{xy}^\infty]}{2(s_1-s_2)}\zeta_2(z_2)$$ (44)

where:

$$\zeta_1(z_1) = \frac{z_1 \pm \sqrt{z_1^2 - r^2(1+s_1^2)}}{r(1+is_1)} \\ \zeta_2(z_2) = \frac{z_2 \pm \sqrt{z_2^2 - r^2(1+s_2^2)}}{r(1+is_2)}$$ (45)

The sign ambiguity in Eqns. (45) may be removed by requiring $|\zeta_1| \leq 1$ and $|\zeta_2| \leq 1$. The complex variables are defined in terms of the real position coordinates according to: $z_1 = x + s_1 y$ and $z_2 = x + s_2 y$. Finally, the displacement field components at Ox and Oy directions are given by:

$$u = 2\text{Re}[p_1\varphi_0(z_1) + p_2\psi_0(z_2)] + x\varepsilon_{xx}^\infty + y\varepsilon_{xy}^\infty \brace v = 2\text{Re}[q_1\varphi_0(z_1) + q_2\psi_0(z_2)] + y\varepsilon_{yy}^\infty + x\varepsilon_{xy}^\infty} \quad (46)$$

with, $$\left.\begin{array}{l} p_1 = a_{11}s_1^2 + a_{12} - a_{16}s_1 \\ p_2 = a_{11}s_2^2 + a_{12} - a_{16}s_2 \\ q_1 = \dfrac{a_{12}s_1^2 + a_{22} - a_{26}s_1}{s_1} \\ q_2 = \dfrac{a_{12}s_2^2 + a_{22} - a_{26}s_2}{s_2} \end{array}\right\} \quad (47)$$

Figure 8:
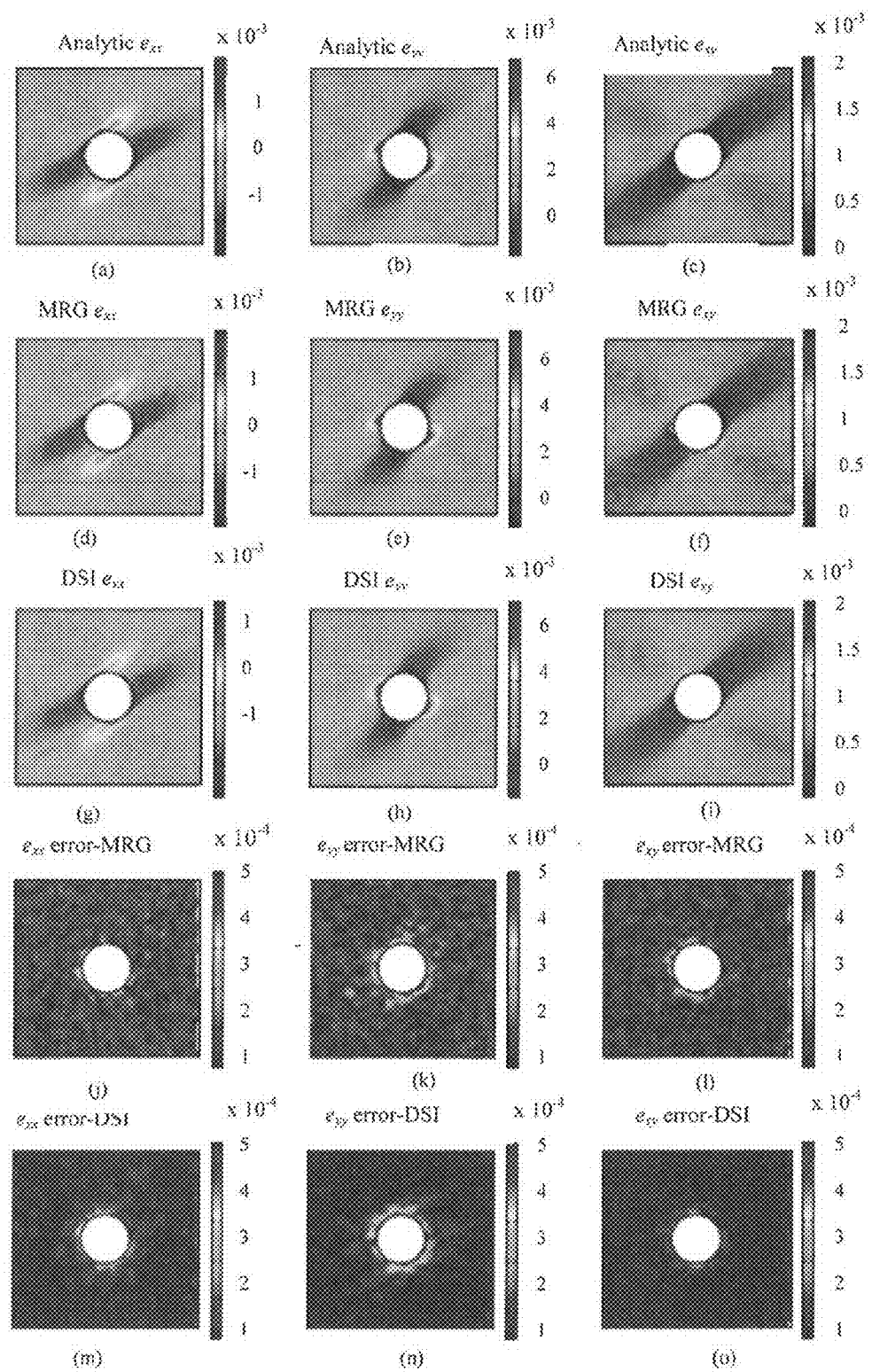
FIG. 8 shows the strain and absolute error contours for the plate of Figure with a nodal noise level of 1×10$^{-2}$ pixels and loading angle of β=45°.

FIG. 8 shows the strain and absolute error contours for nodal noise level of $1 \times 10^{-2}$ pixels and loading angle of $\beta = 45°$. The domain is assumed to span 1600 pixels wide by 1600 pixels in height. (a, b, c): $\epsilon_{xx}$, $\epsilon_{yy}$, $\epsilon_{xy}$ of the analytic solution, (d, e, f): $\epsilon_{xx}$, $\epsilon_{yy}$, $\epsilon_{xy}$ of the synthetic experiment using the MRG method, (g, h, i): $\epsilon_{xx}$, $\epsilon_{yy}$, $\epsilon_{xy}$ of the synthetic experiment using the DSI method, (j, k, l): respective absolute error of the MRG method, (m, n, o): respective absolute error of the DSI method.

Numerical Experiments

In order to compute the fields for the synthetic numerical experiments, the radius of the hole was selected to be $a = 10^{-2}$ m, the stress at infinity $\sigma_\infty = 7 \times 10^5$ Pa, the angle of the major orthotropic axis was $\beta = 45°$ while the extent of the domain of interest (in both the x and y coordinates) was 8a. The material properties were selected to be:

$$\begin{bmatrix} a_{11} & a_{12} & a_{16} \\ a_{12} & a_{22} & a_{26} \\ a_{16} & a_{26} & a_{66} \end{bmatrix} = \begin{bmatrix} 2.245 & -2.732 & 0.000 \\ -2.732 & 9.436 & 0.000 \\ 0.000 & 0.000 & 4.315 \end{bmatrix} \times 10^{-9} \text{Pa}^{-1} \quad (48)$$

The domain was assumed to span 1600 pixels wide by 1600 pixels in height. (a, b, c): $\epsilon_{xx}$, $\epsilon_{yy}$, $\epsilon_{xy}$ of the analytic solution, (d, e, f): $\epsilon_{xx}$, $\epsilon_{yy}$, $\epsilon_{xy}$ of the synthetic experiment using the MRG method, (g, h, i): $\epsilon_{xx}$, $\epsilon_{yy}$, $\epsilon_{xy}$ of the synthetic experiment using the DSI method, (j, k, l): respective absolute error of the MRG method, (m, n, o): respective absolute error of the DSI method.

A total of 2380 randomly distributed nodes were generated using known methods, while the displacement field of Eqn. (46) was used to generate the displaced nodes, with varying levels of noise. Since for the current digital imaging technology and for most practical applications the accuracy in coordinate measurement is approximately at the range of $5 \times 10^{-4}$ to $5 \times 10^{-2}$ pixels, the noise level was chosen to vary from $10^{-4}$ to $10^{-1}$ pixels, assuming the entire domain is mapped on a digital image that is 1600 pixels wide by 1600 pixels high. For the load angle sensitivity trials, the angle $\beta$ was chosen to vary from 0° to 90°, the noise level was kept at $1 \times 10^{-2}$ pixels and the synthetic runs were executed 70 times, in order to also obtain an estimation of the variation of the mean absolute error.

The basis function for MRG was chosen to be of second order (a total of 6 terms), while for the DSI it was chosen to be of first order (a total of 3 terms). This choice was made so that the approximation on strains for both methods is of the same polynomial degree. The domain of support radius was chosen at $3.6 \times 10^{-3}$ m, while the weight function was the one presented in Eqn. (21).

Figure 9:
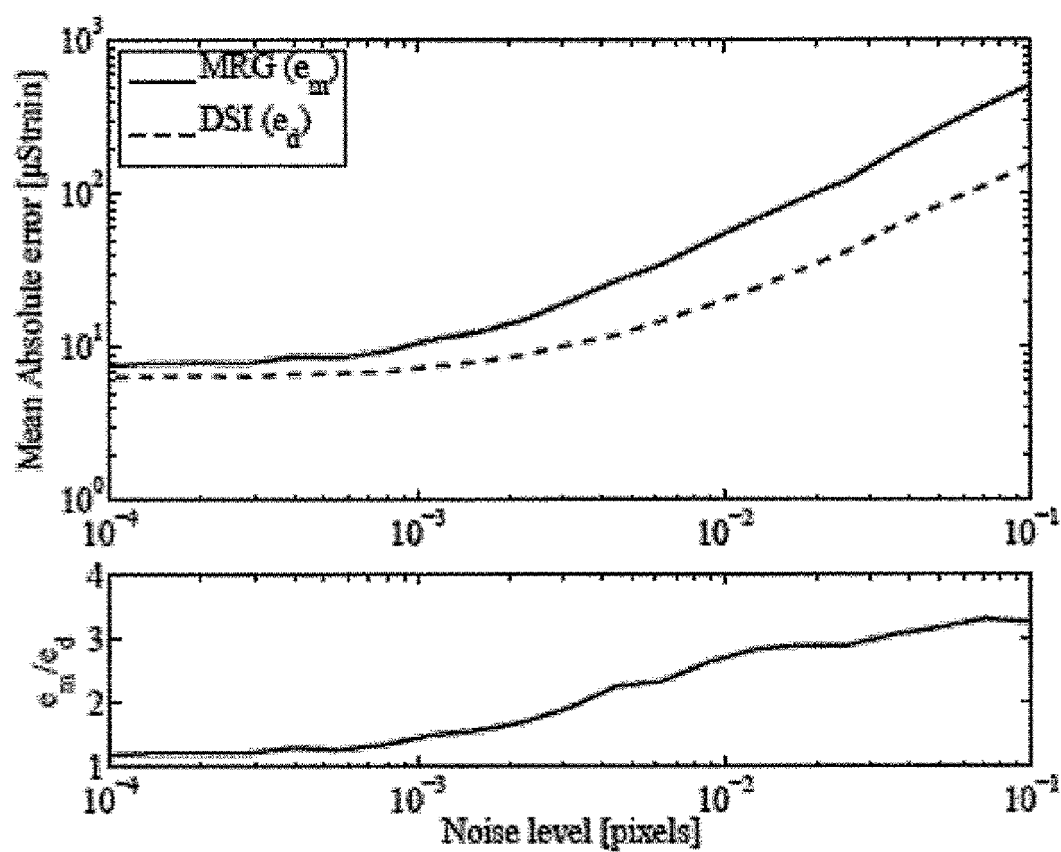
FIG. 9 shows the mean absolute error of $\epsilon_{xx}$ over the interest domain and relative performance of DSI over MRG ($\epsilon_{yy}$, $\epsilon_{xy}$ show similar behavior)

In FIG. 8 the strain contours, as well as the absolute error of the MRG and DSI methods, are plotted. For those plots the level of noise imposed on the node coordinates was $1 \times 10^{-2}$ pixels. It is evident that DSI performed considerably better within the entire domain (FIGS. 8(m), 8(n), and 8(o)) compared to MRG for all strain components. This fact is more evident in FIG. 9, where the mean absolute error of $\epsilon_{xx}$ over the entire domain was plotted for MRG and DSI for various noise levels. The ratio of those errors (bottom graph of FIG. 9) reveals that DSI is about at least 1.2 times more accurate than MRG. In the same graph it can be seen that DSI can be up to 3.3 times more accurate.

Figure 10:
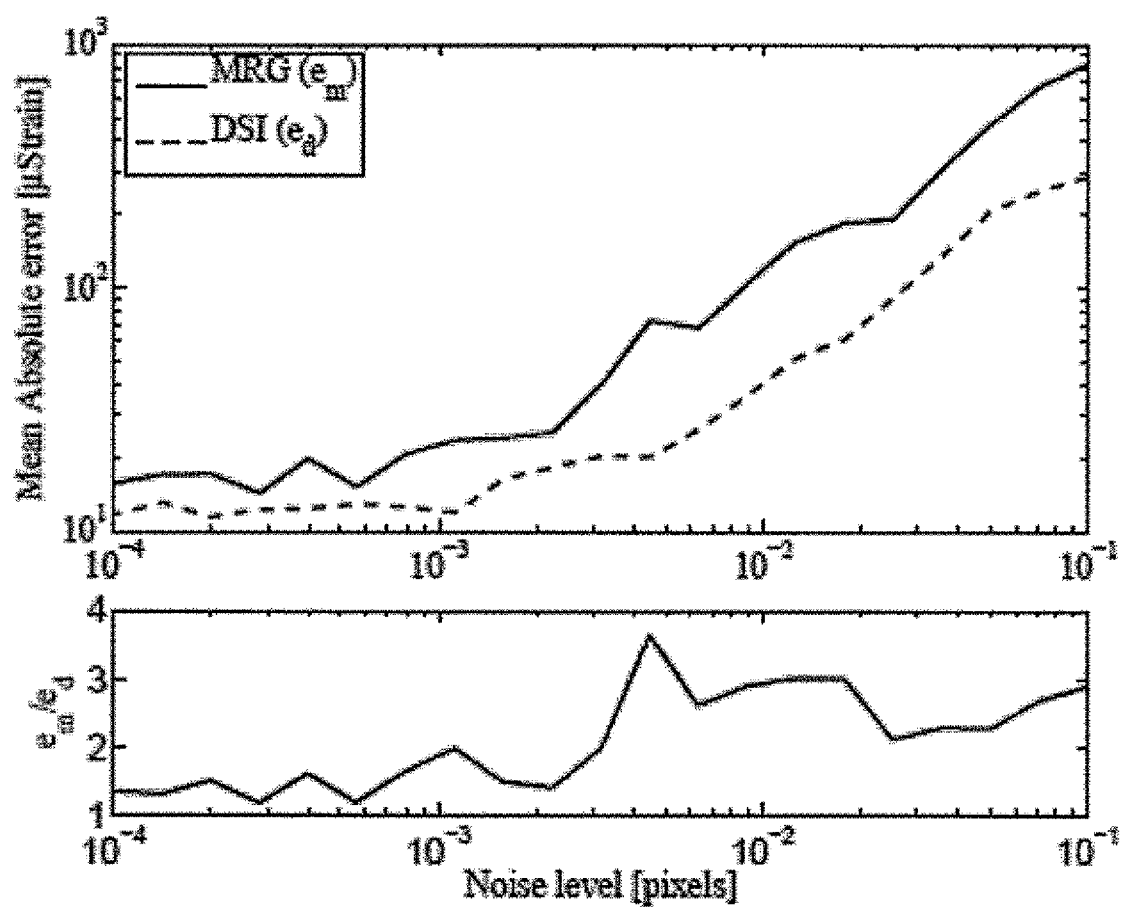
FIG. 10 shows the mean absolute error of $\epsilon_{xx}$ over the hole boundary and relative performance of DSI over MRG ($\epsilon_{yy}$, $\epsilon_{xy}$ show similar behavior)

Similarly, in FIG. 10, the mean absolute error over the boundary of the hole is plotted. In this case as well DSI outperforms MRG by a factor ranging from about 1.2 to about 3.6 times. It is also worthwhile mentioning that DSI performs better with increasing noise levels.

Both methods seem to reach a plateau for noise levels below $2 \times 10^{-3}$, which is anticipated to depend on the spatial density of the nodes. It should be noted that for most practical cases the displacement noise levels are between $5 \times 10^{-3}$ to $10 \times 10^{-3}$, which give the DSI an average performance markup of about 3 times for both error metrics.

Figure 11:
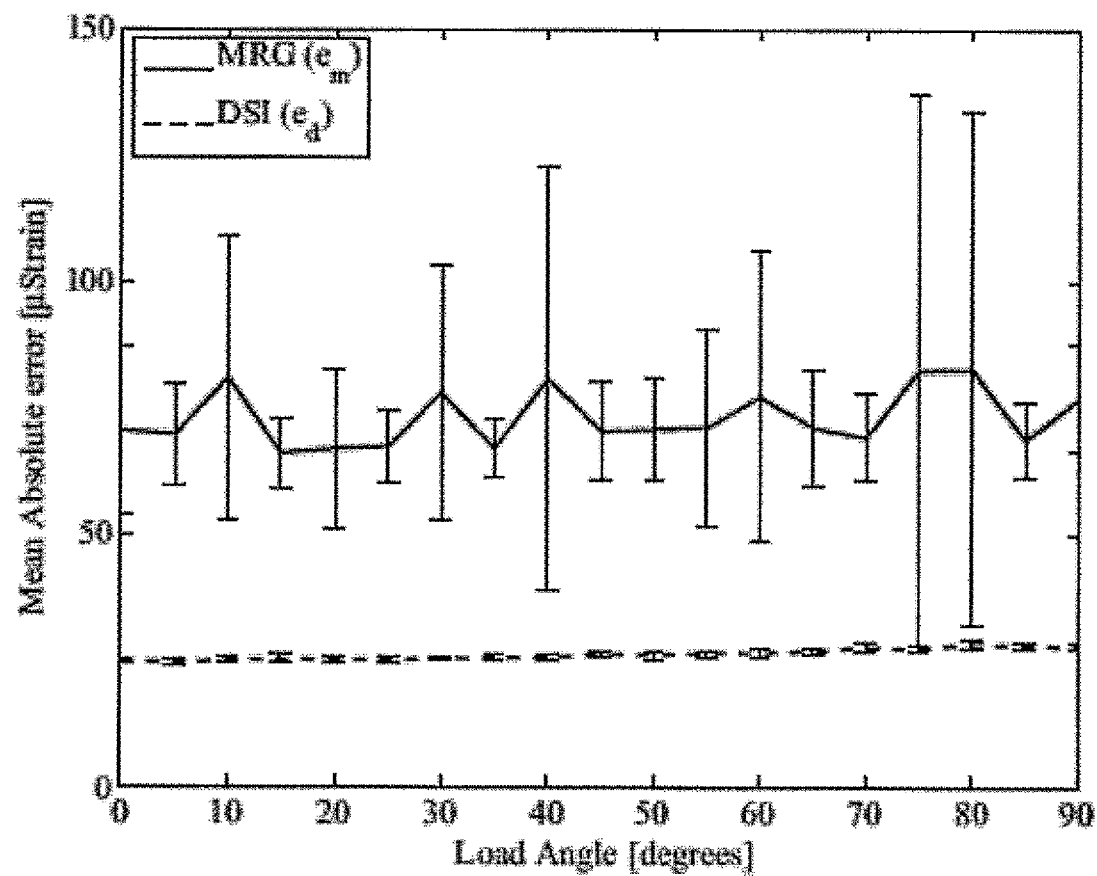
FIG. 11 shows the mean absolute error of $\epsilon_{xx}$ over the entire domain versus load angle ($\epsilon_{yy}$, $\epsilon_{xy}$, show similar behavior).

Finally, in FIG. 11, the mean absolute error of each of the methods is plotted with respect to the loading angle as this induces the strain variability due to the specific nature of the anisotropic elastic problem at hand. For each load angle, 70 trials were performed. The standard deviation is shown as the error bars in the graph. It is worthwhile noting that the standard deviation of the DSI error is very small and the error bars are almost indistinguishable from the trend line. As expected, the average of the mean error is not affected by the load angle, but for the MRG Method its deviation (i.e. the error of the error) is considerably larger. This observation further supports the utilization of the DSI method in applications where the knowledge of the uncertainty of the full field measurements is of importance.

DSI outperformed MRG both on the regions near the domain boundaries, where Full-Field methods traditionally suffer, but also on the rest of the domain of interest. For the chosen medium configuration, DSI was found to be at least 1.2 times more accurate, while there were tests in which it achieved an accuracy improvement of up to 3.6 times. It was established that at the noise levels of the most popular digital imaging devices, DSI outperforms MRG by a factor of 3 in terms of the mean absolute error. DSI also proved to be very robust and numerically stable in terms of mean error deviation, as was shown by repeated numerical experiments under the same image sensor noise levels.

Furthermore, DSI does not make any explicit or implicit assumptions on the continuity of the underlying field, and therefore can be used on media that either cannot be considered continuous, has cracks, otherwise has failed. DSI enables approximation of tensor quantities from directional component measurements, rather than a scalar quantity that is usually the case for typical regression analysis approaches.

Some embodiments of the system may include a deformable body or test specimen, visually patterned in the manner described above, a test device for deforming the body, the image acquisition system, data storage for storing the images and associated information, communications links for transmitting the images or data and associated information to the computer system that implements the processing steps (including the point or pattern matching algorithms, and algorithms for calculating and displaying the full field). Other embodiments may be specifically directed to generating non visible separation data, for example.

Portions of the system operate in a computing operating environment, for example, a specially configured desktop computer, a laptop computer, a mobile computer, a server computer, and the like, in which embodiments of the invention may be practiced. The computer may operationally inter-relate or communicate with digital imaging devices or cameras 12 or 18. Alternatively, the inter-relation may be by transfer of media or data. In some applications, imaging device may include ultrasonography or tomography devices generating equivalent data.

A brief, general description of a suitable computing environment in which embodiments of the invention may be implemented. While the invention will be described in the general context of program modules that execute in conjunction with program modules that run on an operating system on a computer, those skilled in the art will recognize that the invention may also be implemented in combination with other types of computer systems and program modules.

Generally, program modules include routines, programs, components, data structures, and other types of structures that perform particular tasks or implement particular abstract data types. Moreover, those skilled in the art will appreciate that the invention may be practiced with other computer system configurations, including hand-held devices, multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote memory storage devices.

An illustrative operating environment for embodiments of the invention will be described. A computer comprises a general purpose desktop, laptop, handheld, mobile or other type of computer (computing device) capable of executing one or more application programs. The computer includes at least one central processing unit ("CPU"), a system memory, including a random access memory ("RAM") and a read-only memory ("ROM"), and a system bus that couples the memory to the CPU. A basic input/output system containing the basic routines that help to transfer information between elements within the computer, such as during startup, is stored in the ROM. The computer further includes a mass storage device for storing an operating system, application programs, and other program modules.

The mass storage device is connected to the CPU through a mass storage controller (not shown) connected to the bus. The mass storage device and its associated computer-readable media provide non-volatile, non-transient storage for the computer. Although the description of computer-readable media contained herein refers to a mass storage device, such as a hard disk or CD-ROM drive, it should be appreciated by those skilled in the art that computer-readable media can be any available non-transient media that can be accessed or utilized by the computer, such as storage access via a network or the interne.

By way of example, and not limitation, computer-readable media may comprise computer storage media and communication media. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology, CD-ROM, digital versatile disks ("DVD"), or other optical storage, magnetic cassettes, magnetic tape, magnetic disk storage or other magnetic storage devices, or any other medium which can be used to store the desired information and which can be accessed by the computer. Such media does not extend to transient signals, for example.

According to one embodiment, the computational workbench for visualizing the full field characteristics of deformable bodies may include a number of program modules.

According to various embodiments of the invention, the computer may operate in a networked environment using logical connections to remote computers through a network, such as a local network, the Internet, etc. for example. The computer may connect to the network through a network interface unit connected to the bus. It should be appreciated that the network interface unit may also be utilized to connect to other types of networks and remote computing systems. The computer may also include an input/output controller for receiving and processing input from a number of other devices, including a keyboard, mouse, etc. (not shown). Similarly, an input/output controller may provide output to a display screen, a printer, or other type of output device.

As mentioned briefly above, a number of program modules and data files may be stored in the mass storage device and RAM of the computer, including an operating system suitable for controlling the operation of a networked personal computer. The mass storage device and RAM may also store one or more program modules. In particular, the mass storage device and the RAM may store application programs, such as a software application, for example, a word processing application, a spreadsheet application, a slide presentation application, a database application, etc.

It should be appreciated that various embodiments of the present invention may be implemented as a sequence of computer implemented acts or program modules running on a computing system and/or as interconnected machine logic circuits or circuit modules within the computing system. The implementation is a matter of choice dependent on the performance requirements of the computing system implementing the invention. Accordingly, logical operations including related algorithms can be referred to variously as operations, structural devices, acts or modules. It will be recognized by one skilled in the art that these operations, structural devices, acts and modules may be implemented in software, firmware, special purpose digital logic, and any combination thereof without deviating from the spirit and scope of the present invention as described herein.

What is claimed is:

1. A computer-implemented method for determining strain characteristics in a vicinity of a point of interest $w=\{x_w, y_w\}^T$ in two parametric dimensions embedded in a two or three dimensional space, wherein the point of interest w is part of a deformable domain or body having a plurality of features which may be represented as a node pattern of n nodes, the method comprising:

receiving a first set of captured data of a plurality of features and representing the plurality of features by nodes indexed by i or j in the domain in an un-deformed configuration;

receiving a second set of captured data of the plurality of features represented by nodes i,j in the domain in a deformed configuration;

measuring engineering strains $e_{i,j}$ between a plurality of node combinations in the vicinity of w to produce $e_w=\{e_{21}, e_{31}, \ldots e_{42} \ldots, e_{n(n-1)}\}^T$; and applying an approximation or interpolation to the engineering strains $e_{i,j}$ to approximate strain $\epsilon^h$ in the vicinity of w.

2. The method of claim 1, wherein the approximation defines an overdetermined system of equations.

3. The method of claim 1, wherein the moving least squares approximation expresses strain $\epsilon^h$ in two parametric dimensions embedded in a two or three dimensional space by $$\left.\begin{array}{l} \varepsilon_{xx}^h(w) \equiv \varepsilon_{xx}^h(w; w) = \Phi_{xx}(w)e_w \\ \varepsilon_{yy}^h(w) \equiv \varepsilon_{yy}^h(w; w) = \Phi_{yy}(w)e_w \\ \varepsilon_{xy}^h(w) \equiv \varepsilon_{xy}^h(w; w) = \Phi_{xy}(w)e_w \end{array}\right\}$$

where $\Phi_\alpha(w)=p^T(w)M_\alpha(w)$ are shape functions of strain components for the vicinity of w for $\alpha$=xx, yy, xy.

4. The method of claim 3, wherein the first and second sets of captured data each being a digital images, and further comprising identifying real mean strain $e_{i,j}$ between a number of node combinations by $$e_{ij} = \overline{\varepsilon_{xx'}}(x_i, x_j) = \frac{l'_{ij} - l_{ij}}{l_{ij}} = \frac{l'_{ij}}{l_{ij}} - 1 = \left|\frac{x'_i - x'_j}{x_i - x_j}\right| - 1,$$
$$j = 1 \ldots n-1, i = 2 \ldots n, i > j$$

where $x_i$, $x_j$ are vectors representing a position of nodes i,j at the un-deformed configuration and $x'_i$, $x'_j$ are the same vectors in the deformed configuration.

5. The method of claim 1, wherein the first and second sets of captured data comprise a first and second sequence of images from at least two digital imaging devices positioned facing the node pattern.

6. The method of claim 1, wherein the first and second sets of captured data are digital images and the plurality of features are visible.

7. The method of claim 1, wherein each of said n nodes comprises a centroid of a visible dot or feature.

8. The method of claim 1, wherein the first and second sets of captured data are the first and second digital images respectively, the method further comprising identifying the node pattern in the first and second digital images via one or more image processing steps.

9. The method of claim 8, wherein said one or more image processing steps comprise eliminating irregular objects from said first and second digital images based on the objects having an intensity below a threshold value of intensity, a pixel area outside a predetermined range, an out-of-range aspect ratio, an out-of-range moment of inertia, an out-of-range major axes direction, or an out-of-range compactness ratio.

10. The method of claim 1, wherein the first and second sets of captured data are the first and second images respectively, wherein said receiving said first and second images comprises digitally photographing a deformable body during deformation with two or more cameras for generating image data and communicating the image data to a computer processor having a memory.

11. A system for determining strain characteristics in a vicinity of a point of interest $w=\{x_w, y_w\}^T$ in two parametric dimensions embedded in a two or three dimensional space for a deformable domain having a plurality of features which may be represented as a node pattern of n nodes, the system comprising:

at least two imaging devices arranged facing the plurality of features at different angles to the surface of the deformable domain for acquiring a first image of the plurality of features in the domain in an un-deformed configuration and a second image of the plurality of features in the domain in a deformed configuration; and a computer processor having programmed instructions thereon for (a) representing the plurality of features by nodes i,j;

(b) measuring engineering strains $e_{i,j}$ between a plurality of node combinations in the vicinity of w to produce $e_w=\{e_{21}, e_{31}, \ldots e_{42} \ldots, e_{n(n-1)}\}^T$; and (c) applying an approximation or interpolation to the engineering strains $e_{i,j}$ to approximate strain $\epsilon^h$ in the vicinity of w.

12. The system of claim 11, wherein the approximation defines an overdetermined system.

13. The system of claim 11, wherein the approximation expresses strain by $$\left.\begin{array}{l} \varepsilon_{xx}^h(w) \equiv \varepsilon_{xx}^h(w; w) = \Phi_{xx}(w)e_w \\ \varepsilon_{yy}^h(w) \equiv \varepsilon_{yy}^h(w; w) = \Phi_{yy}(w)e_w \\ \varepsilon_{xy}^h(w) \equiv \varepsilon_{xy}^h(w; w) = \Phi_{xy}(w)e_w \end{array}\right\}$$

where $\Phi_\alpha(w)=p^T(w)M_\alpha(w)$ are shape functions of strain components for the vicinity of w for $\alpha$=xx, yy, xy.

14. The system as in claim 11, the processor having further instructions for corresponding nodes in an un-deformed configuration with nodes in a deformed configuration to form the plurality of node combinations, such that where $x_i$, $x_j$ are vectors representing a position of nodes i,j at the un-deformed configuration and $x'_i$, $x'_j$ are the same vectors in the deformed configuration.

15. The system as in claim 14, the processor having further instructions for identifying real mean strain $e_{i,j}$ between a number of node combinations by:

$$e_{ij} = \overline{\varepsilon_{xx'}}(x_i, x_j) = \frac{l'_{ij} - l_{ij}}{l_{ij}} = \frac{l'_{ij}}{l_{ij}} - 1 = \left|\frac{x'_i - x'_j}{x_i - x_j}\right| - 1,$$
$$j = 1 \ldots n-1, i = 2 \ldots n, i > j.$$

16. The system as in claim 11, further comprising: a display connected to the processor, and the processor having further instructions for displaying and storing the first and second images and a graphical representation of strain in the domain.

17. The system of claim 11, wherein the processor comprises instructions for determining the node pattern stereoscopically.

18. A computer-implemented method for measuring strain characteristics in a vicinity of a point of interest $w=\{x_w, y_w\}^T$ in two parametric dimensions embedded in a two or three dimensional space for a deformable domain having a plurality of features which may be represented as a node pattern of n nodes, the method comprising:

receiving separation-data for a plurality of nodes i,j in the domain in an un-deformed configuration;

receiving separation data for the plurality of nodes i,j in the domain in a deformed configuration;

measuring engineering strains $e_{i,j}$ between a number of node combinations in the vicinity of w to produce $e_w = \{e_{21}, e_{31}, \ldots e_{42} \ldots, e_{n(n-1)}\}^T$; and
approximating strain $\epsilon^h$ in the vicinity of w by $$\left. \begin{array}{l} \varepsilon_{xx}^h(w) \equiv \varepsilon_{xx}^h(w;w) = \Phi_{xx}(w)e_w \\ \varepsilon_{yy}^h(w) \equiv \varepsilon_{yy}^h(w;w) = \Phi_{yy}(w)e_w \\ \varepsilon_{xy}^h(w) \equiv \varepsilon_{xy}^h(w;w) = \Phi_{xy}(w)e_w \end{array} \right\}$$

where $\Phi_\alpha(w) = p^T(w) M_\alpha(w)$ are shape functions of strain components in the vicinity of w for $\alpha = xx, yy, xy$.

19. The method of claim 18, further comprising identifying real mean strain $e_{i,j}$ between a number of node combinations by:

$$e_{ij} = \overline{\varepsilon_{xx'}}(x_i, x_j) = \frac{l'_{ij} - l_{ij}}{l_{ij}} = \frac{l'_{ij}}{l_{ij}} - 1 = \left| \frac{x'_i - x'_j}{x_i - x_j} \right| - 1,$$

-continued $$j = 1 \ldots n-1, i = 2 \ldots n, i > j$$

where $x_i, x_j$ are vectors representing a position of nodes i,j at the un-deformed configuration and $x'_i, x'_j$ are the same vectors in the deformed configuration.

20. The method of claim 18, wherein the separation data is derived from neighboring markers using one of ultrasonography or X-ray tomography imaging or digital imaging of any kind.

21. The method of claim 1, wherein the applying comprises applying a spatial moving least squares approximation to the engineering strains.

22. The system of claim 11, wherein the applying comprises applying a spatial moving least squares approximation to the engineering strains.

23. The method of claim 1, wherein the first set of captured data is a first image in the second set of captured data is a second image.

* * * * *